US010813954B2

(12) United States Patent
Lee et al.

(10) Patent No.: US 10,813,954 B2
(45) Date of Patent: Oct. 27, 2020

(54) PHARMACEUTICAL COMPOSITION FOR TREATING DIABETES, COMPRISING PANCREATIC ISLET CELLS AND ELASTIN-LIKE ARTIFICIAL EXTRACELLULAR MATRIX

(71) Applicant: DAEGU GYEONGBUK INSTITUTE OF SCIENCE AND TECHNOLOGY, Daegu (KR)

(72) Inventors: Kyeong Min Lee, Daegu (KR); Won Bae Jeon, Daegu (KR); Jung Hee Kim, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 15/773,496

(22) PCT Filed: Nov. 3, 2016

(86) PCT No.: PCT/KR2016/012611
§ 371 (c)(1),
(2) Date: May 3, 2018

(87) PCT Pub. No.: WO2017/078439
PCT Pub. Date: May 11, 2017

(65) Prior Publication Data

US 2018/0318357 A1 Nov. 8, 2018

(30) Foreign Application Priority Data

Nov. 3, 2015 (KR) ........................ 10-2015-0154093

(51) Int. Cl.

| | |
|---|---|
| ***A61K 35/39*** | (2015.01) |
| ***A61K 38/39*** | (2006.01) |
| ***C07K 14/78*** | (2006.01) |
| ***C07K 7/00*** | (2006.01) |
| ***A61P 3/10*** | (2006.01) |

(52) U.S. Cl.
CPC .............. *A61K 35/39* (2013.01); *A61K 38/39* (2013.01); *A61P 3/10* (2018.01); *C07K 7/00* (2013.01); *C07K 14/78* (2013.01)

(58) Field of Classification Search
None
See application file for complete search history.

(56) References Cited

FOREIGN PATENT DOCUMENTS

| | | |
|---|---|---|
| KR | 10-1350900 | 1/2014 |
| KR | 10-1429346 | 8/2014 |
| KR | 20140103985 | 8/2014 |

OTHER PUBLICATIONS

Blomeier et al., "Polymer Scaffolds as Synthetic Microenvironments for Extrahepatic Islet Transplantation," Transplant. 82:452-459 (2006) (Year: 2006).*

International Search Report and Written Opinion issued in International Patent Application No. PCT/KR2016/012611, dated Feb. 24, 2017.

Jeon et al., "Stimulation of fibroblasts and neuroblasts on a biomimetic extracellular matrix consisting of tandem repeats of the elastic VGVPG domain and RGD motif" *J. Biomed. Mater. Res. A*, 97:152-157, (2011).

Kim et al., "Pancreas-like extracellular matrix scaffold for successful pancreatic islet transplantation," *Macromolecular Research*, 22(6):575-582, (2014).

Labat-Robert, "Introduction: matrix biology in the 21$^{st}$ century, From a static-rheological role to a dynamic-signaling function," *Pathol Biol.*, 53:369-371, (2005).

Lee et al., "Effects of Arg-Gly-Asp-modified elastin-like polypeptide on pseudoislet formation via up-regulation of cell adhesion molecules and extracellular matrix proteins," *Acta Biomater*, 9(3):5600-8, (2013).

Rosso et al., "From Cell-ECM Interactions to Tissue Engineering," *Journal of Cellular Physiology*, 199:174-180, (2004).

* cited by examiner

*Primary Examiner* — Julie Ha
*Assistant Examiner* — Kristina M Hellman
(74) *Attorney, Agent, or Firm* — Hauptman Ham, LLP

(57) ABSTRACT

The present invention relates to a pharmaceutical composition for treating diabetes, which includes a pancreatic islet cell and an elastin-like artificial extracellular matrix (REP), and more particularly, to a pharmaceutical composition for treating diabetes, in which pancreatic islet cells are reacted with an elastin-like artificial extracellular matrix and then the resulting cells are administered along with the elastin-like artificial extracellular matrix, thus increasing a survival rate of the transplanted pancreatic islet cells, rapidly restoring a blood glucose level to normal, and maintaining the restored blood glucose level for a long period of time, and, accordingly, diabetes may be more effectively treated.

4 Claims, 14 Drawing Sheets

Specification includes a Sequence Listing.

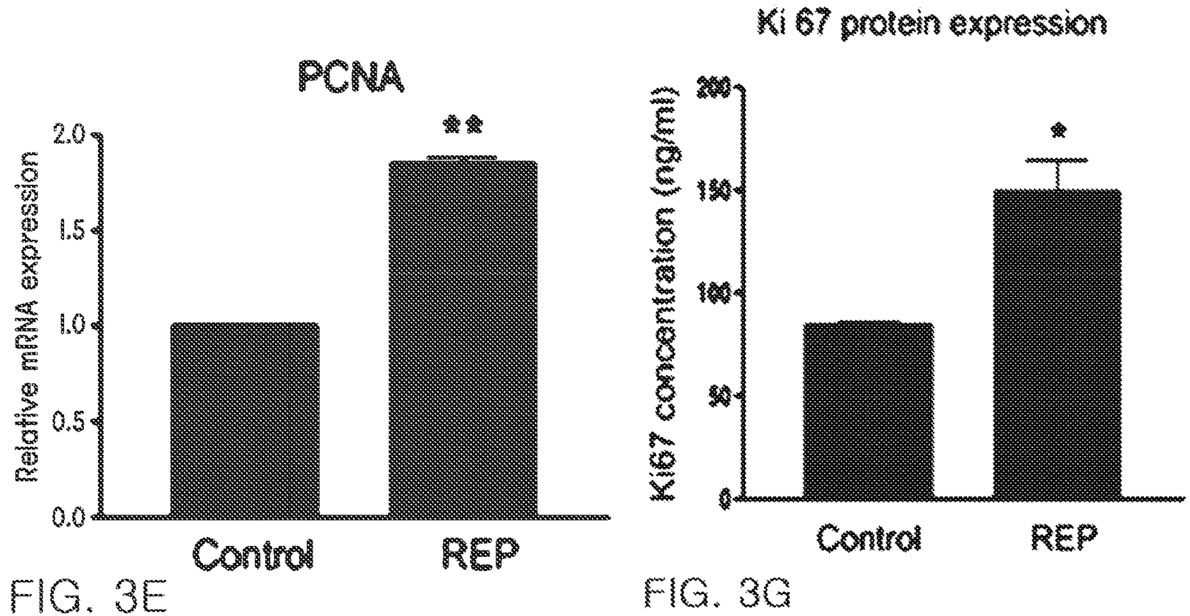
FIG. 3E
FIG. 3G
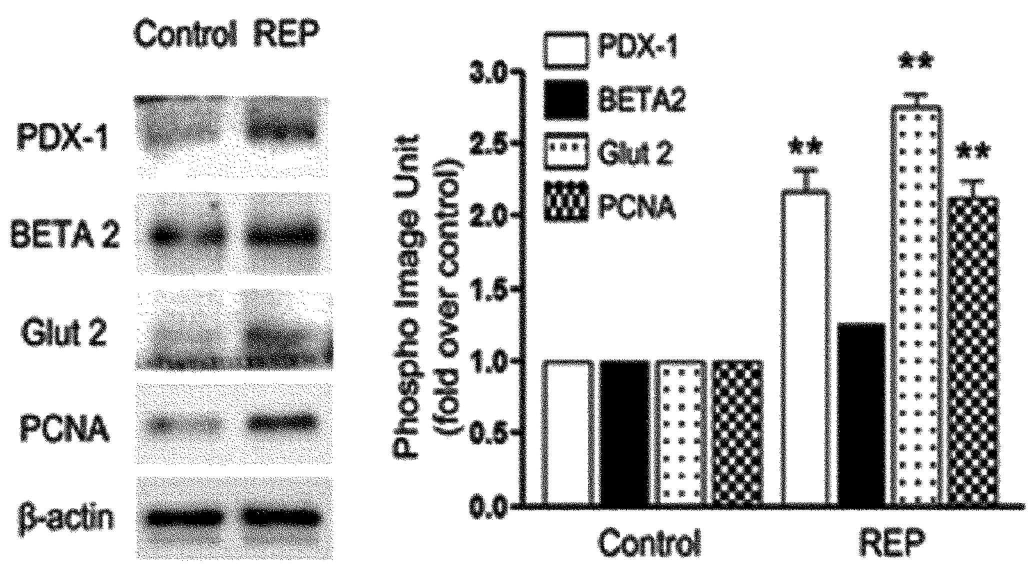
FIG. 3F

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: Elastin-like polypeptide

<400> SEQUENCE: 1

Val Gly Val Pro Gly
1               5


<210> SEQ ID NO 2
<211> LENGTH: 3
<212> TYPE: PRT
<213> ORGANISM: Artificial
<220> FEATURE:
<223> OTHER INFORMATION: Ligand

<400> SEQUENCE: 2

Arg Gly Asp
1


<210> SEQ ID NO 3
<211> LENGTH: 17
<212> TYPE: PRT
<213> ORGANISM: Artificial
<220> FEATURE:
<223> OTHER INFORMATION: Multiblock biopolymer(REP)
<220> FEATURE:
<221> NAME/KEY: REPEAT
<222> LOCATION: (5)..(14)
<223> OTHER INFORMATION: 10, 12, 15 or 20 sequence repetitions
<220> FEATURE:
<221> NAME/KEY: REPEAT
<222> LOCATION: (10)..(14)
<223> OTHER INFORMATION: 6 sequence repetitions

<400> SEQUENCE: 3

Thr Gly Pro Gly Val Gly Arg Gly Asp Val Gly Val Pro Gly Trp Pro
1               5                   10                  15

Cys


<210> SEQ ID NO 4
<211> LENGTH: 10
<212> TYPE: PRT
<213> ORGANISM: Artificial
<220> FEATURE:
<223> OTHER INFORMATION: Multiblock biopolymer(REP)
<220> FEATURE:
```

-continued

```
<221> NAME/KEY: REPEAT
<222> LOCATION: (1)..(10)
<223> OTHER INFORMATION: 10, 12, 15 or 20 sequence repetitions
<220> FEATURE:
<221> NAME/KEY: REPEAT
<222> LOCATION: (6)..(10)
<223> OTHER INFORMATION: 6 sequence repetitions

<400> SEQUENCE: 4

Val Gly Arg Gly Asp Val Gly Val Pro Gly
1               5                   10
```

PHARMACEUTICAL COMPOSITION FOR TREATING DIABETES, COMPRISING PANCREATIC ISLET CELLS AND ELASTIN-LIKE ARTIFICIAL EXTRACELLULAR MATRIX

CROSS-REFERENCE TO RELATED APPLICATIONS

This application is a national phase application under 35 U.S.C. § 371 of International Application No. PCT/KR2016/012611, filed Nov. 3, 2016, which claims priority to and the benefit of Korean Patent Application No. 10-2015-0154093, filed on Nov. 3, 2015, the disclosures of which are incorporated herein by reference in their entireties.

FIELD OF THE DISCLOSURE

The present invention relates to a pharmaceutical composition for treating diabetes, which includes pancreatic islet cells and an elastin-like artificial extracellular matrix (REP), and more particularly, to a pharmaceutical composition for treating diabetes, in which pancreatic islet cells are reacted with an elastin-like artificial extracellular matrix and then the resulting cells are administered along with the elastin-like artificial extracellular matrix, thus increasing a survival rate of the transplanted pancreatic islet cells, rapidly restoring a blood glucose level to normal, and maintaining the restored blood glucose level for a long period of time, and, accordingly, diabetes may be more effectively treated.

DESCRIPTION OF RELATED ART

Diabetes refers to a group of metabolic disorders having multiple etiologies and characterized by chronic hyperglycemia due to defects in insulin secretion or insulin action, and when abnormally high blood glucose levels are continued for a long period of time, various complications occur due to chronic metabolic disorders and chronic vascular injury caused accordingly.

About 5% of the world population suffers from diabetes, a representative adult metabolic disorder, and thus human and economic losses due to this are tremendous. Most diabetic patients take oral therapeutic agents, but a safe therapeutic agent has not yet been developed. Insulin resistance is known to be the most important pathological cause, but the exact mechanism of diabetes is still unknown, and it is known that diabetes is caused by multiple etiologies including genetic predisposition and environmental factors.

Insulin therapy has been used for the treatment of patients with insulin-dependent diabetes (type 1 diabetes) accompanied by an insulin secretion disorder, but various complications including renal failure, neuropathy, blindness, and myocardial infarction are caused, and thus there are therapeutic limitations. Thus, to fundamentally treat type 1 diabetes, pancreas transplantation or pancreatic islet cell transplantation should be performed. Currently, transplantation surgery of the pancreas and pancreatic islet cells from a brain-dead patient is performed, but it lags behind that in the western world and there are an absolute lack of brain-dead patients as donors and lack of awareness about pancreatic islet transplantation.

Pancreas transplantation requires the administration of an immunosuppressant after transplantation surgery, and there are problems such as surgical side effects, complications, and transplant rejection, but the transplantation of pancreatic islet cells is relatively advantageous in that surgery is convenient and an immune injection response is reduced after transplantation. However, even in a pancreatic islet cell transplantation process, an extracellular matrix is destroyed in a process of isolating pancreatic islet cells from the pancreas, and thus cell activity is decreased, and a cell fixation rate and a cell survival rate are reduced after pancreatic islet cell transplantation.

Meanwhile, the extracellular matrix (ECM) was first found about 100 years ago and was initially known to play a structural role as a simple intercellular connector (Pathol Biol.) (2005) 53, 369-371). However, it has been confirmed that beyond this, the extracellular matrix plays a very important role as a cell physiological regulator, such as cell division, differentiation, and death. In particular, the importance of extracellular matrices has recently been more emphasized for cell therapy and regenerative medicine, which have been combined with embryonic stem cells or adult stem cells. In addition, it is also of great importance for tissue engineering studies that try to create tissues by culturing cells in biomaterials that mimic extracellular matrices.

The extracellular matrix is the product of cells that constitute each tissue as needed. Thus, the extracellular matrix consists of different components according to tissue and has specific physical properties. Generally, the extracellular matrix mainly consists of structural proteins such as collagen or elastin, and in the extracellular matrix, polysaccharides such as glycosaminoglycan (GAG), and adhesive proteins that aid in adhesion of cells are fixed, and various biochemical factors such as growth factors are distributed while being transferred (J Cell Physiol. (2004) 199, 174-80).

Extracellular matrices extracted directly from animal tissues may be the best choice for repeated culturing of live cells on a tissue culture plate in a microhabitat environment. For example, Matrigel or Amgel obtained from rat sarcomas or human amniotic cells has been extensively developed for the analysis of various cellular activities, and has also contributed in part to understanding the behavior of tumor cells. However, specimens of naturally derived ECMs are complicated, have limitations in high yield and mass production, and are also expensive. Thus, there has recently been a growing interest in artificial ECMs that appropriately mimic the physical environment of ECMs.

It has been known that a TGPG[VGRGD(VGVPG)$_6$]$_{20}$WPC (SEQ ID NO:3) multi-block biopolymer (REP), prepared through repeated fusion of an elastin valine-glycine-valine-proline-glycine (VGVPG) (SEQ ID NO:1) pentapeptide, which is one of the elastin-like polypeptides (ELPs), and an arginine-glycine-aspartate (RGD) (SEQ ID NO:2) ligand, is effective in tissue regeneration (Jeon et al., J. Biomed. Mater Res. A, 97:152, 2011; Korean Patent Registration No. 1350900). One of the advantages of the REP is that in response to a temperature change, the solubilized REP disrupts coacervates into hydrophobic materials at a particular transition temperature (Tt) or higher.

In the prior art, although Korean Patent Registration No. 10-1429346 discloses a method of culturing an artificial pancreatic islet, including coating a plate with an elastin-like artificial extracellular matrix, particularly an arginine-glycine-aspartate (RGD) (SEQ ID NO: 2)-elastin like polypeptide (ELP) and culturing pancreatic cells thereon, the RGD (SEQ ID NO: 2)-ELP was used only for culturing pancreatic cells and therapeutic effects obtained when the isolated pancreatic islet cells are reacted with the RGD (SEQ ID NO: 2)-ELP and then administered to diabetic patients along with the RGD (SEQ ID NO: 2)-ELP were not mentioned.

Therefore, as a result of having made intensive efforts to enhance decreased cell activity, which had been exhibited after the isolation of pancreatic islet cells, and a cell fixing rate and a survival rate after transplantation, the inventors of the present invention researched the possibility of a REP matrix and verified that the viability and activity of transplanted pancreatic islet cells could be maintained by reacting isolated pancreatic islet cells with a REP and administering the REP along with the resulting pancreatic islet cells to diabetic patients, thereby maximizing transplantation success rates, thus completing the present invention.

SUMMARY OF THE INVENTION

The present invention has been made to solve the conventional problems as described above, and an object of the present invention is to provide a pharmaceutical composition for treating diabetes, including: a pancreatic islet cell; and an elastin-like artificial extracellular matrix (REP) prepared through repeated fusion of an elastin-like polypeptide and a ligand.

The present invention also provides a method of preventing or treating diabetes, including administering, to an individual in need of the treatment of diabetes, a pancreatic islet cell; and an elastin-like artificial extracellular matrix (REP) prepared through repeated fusion of an elastin-like polypeptide and a ligand.

In addition, the present invention relates to a use of a pancreatic islet cell; and an elastin-like artificial extracellular matrix prepared through repeated fusion of an elastin-like polypeptide and a ligand, for the preparation of a cellular therapeutic agent for treating diabetes.

To address the above-described problems of the present invention, the present invention provides a pharmaceutical composition for treating diabetes, including: a pancreatic islet cell; and an elastin-like artificial extracellular matrix (REP) prepared through repeated fusion of an elastin-like polypeptide and a ligand.

In an exemplary embodiment of the present invention, the pancreatic islet cell may be isolated from the pancreas of an individual selected from the group consisting of a human, a mouse, a rat, a pig, a rabbit, a guinea pig, a hamster, a dog, a cat, a cow, and a goat.

In another exemplary embodiment of the present invention, the elastin-like polypeptide may be an elastin valine-glycine-valine-proline-glycine (VGVPG) (SEQ ID NO: 1) polypeptide.

In another exemplary embodiment of the present invention, the ligand may be arginine-glycine-aspartate (RGD) (SEQ ID NO: 2).

In another exemplary embodiment of the present invention, the elastin-like artificial extracellular matrix may be [VGRGD(VGVPG)6]n where n=10, 12, 15, or 20 (SEQ ID NO: 4).

In another exemplary embodiment of the present invention, the pharmaceutical composition may include 800 to 2,000 pancreatic islet cells; and 0.5 μM to 10 μM of an elastin-like artificial extracellular matrix.

In another exemplary embodiment of the present invention, the diabetes may be type 1 diabetes.

The present invention also provides a method of preventing or treating diabetes, including administering, to an individual in need of the treatment of diabetes, a pancreatic islet cell; and an elastin-like artificial extracellular matrix (REP) prepared through repeated fusion of an elastin-like polypeptide and a ligand.

The present invention also relates to a use of a pancreatic islet cell; and an elastin-like artificial extracellular matrix prepared through repeated fusion of an elastin-like polypeptide and a ligand, for the preparation of a cellular therapeutic agent for treating diabetes.

A pharmaceutical composition for treating diabetes of the present invention, which includes a pancreatic islet cell; and an elastin-like artificial extracellular matrix (REP) prepared through repeated fusion of an elastin-like polypeptide and a ligand, increases the survival rate of pancreatic islet cells after transplantation, rapidly restores a blood glucose level to normal, and enables long-term maintenance of the blood glucose level. Thus, a method of transplanting pancreatic islet cells by using an elastin-like artificial extracellular matrix provides potential as a transplantation tool for treating type 1 diabetes.

BRIEF DESCRIPTION OF THE DRAWINGS

FIGS. 1A to 1D illustrate confirmation results of characteristics of a multi-block biopolymer (REP), wherein FIG. 1A illustrates the absorbance of a REP, FIG. 1B illustrates a coagulation degree of the REP in a coacervate state, FIG. 1C illustrates measurement results of the degree of inverse phase transition of Fam-REP, and FIG. 1D illustrates measurement data for a change in absorbance according to wavelength of the Fam-REP.

FIGS. 3A to 3G: FIGS. 3A, 3B, and 3D are graphs showing the gene expression of PDX-1, BETA2, and Glut2, respectively, which are transcription factors that regulate insulin gene expression of a pancreatic islet reacted with a REP, FIGS. 3C and 3E are graphs showing the gene expression of Ki67 and PCNA, respectively, which are cell growth markers, and FIGS. 3F and 3G are graphs showing the protein expression of PDX-1, BETA2, Glut2, PCNA, and Ki67.

FIGS. 4A to 4E illustrate verification results of the activity of Akt and foxo1 phosphorylation induced by a REP in a pancreatic beta cell line and pancreatic islet cells, wherein FIG. 4A is a graph showing verification results of Akt phosphorylation activated by a REP, fibronectin (FN), and laminin (LN) in the pancreatic beta cell line; FIG. 4B is a graph showing verification results of Akt and foxo1 phosphorylation activated by a REP in the pancreatic islet cells; FIG. 4C illustrates fluorescence microscope images showing intracellular migration of Akt and foxo1 induced by a REP in the pancreatic islet cells; and FIGS. 4D and 4E are graphs showing verification results of Akt and foxo1 phosphorylation regulated by wortmannin, which is an Akt phosphorylation inhibitor, and insulin secretion changes.

FIGS. 5A to 5E illustrate verification results of ERK phosphorylation activated by a REP in a pancreatic beta cell line and pancreatic islet cells, wherein FIGS. 5A and 5B are graphs showing verification results of ERK phosphorylation activated by the REP in the pancreatic beta cell line and the pancreatic islet cells; FIG. 5C is a graph showing results of verifying that the ERK phosphorylation was inhibited by PD98059, which is an ERK phosphorylation inhibitor; and FIGS. 5D and 5E are graph showing results of confirming that a cell growth rate and cell adhesion were regulated by an ERK phosphorylation inhibitor.

DETAILED DESCRIPTION OF THE INVENTION

Figure 1A:
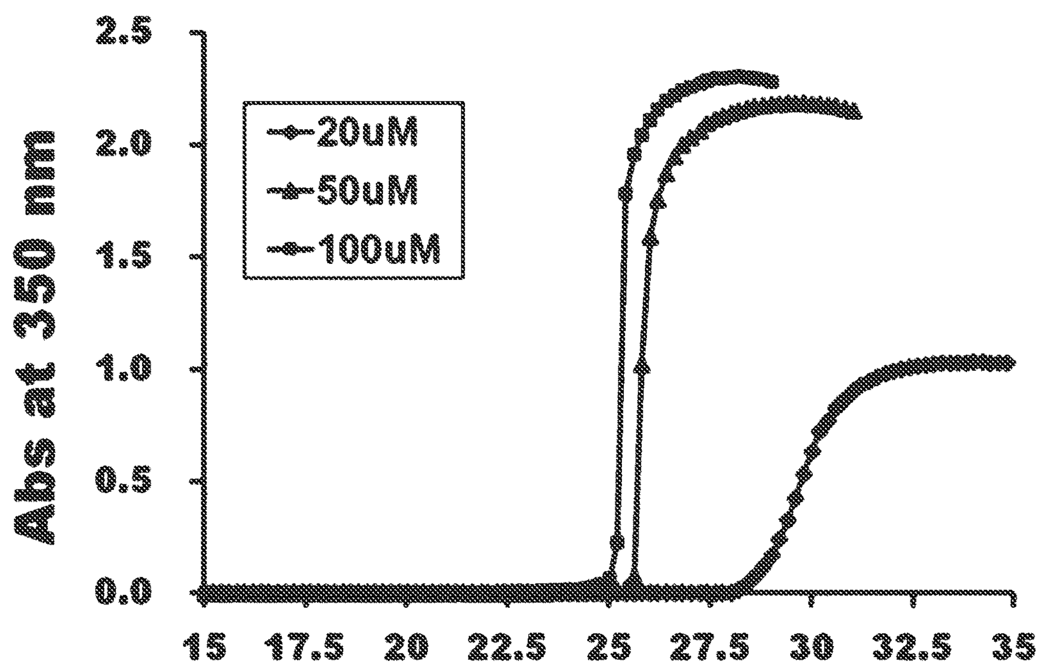

Hereinafter, the present invention will be described in more detail.

As described above, even in a pancreatic islet cell transplantation process, an extracellular matrix is destroyed in a process of isolating pancreatic islet cells from the pancreas, and thus cell activity is decreased, and a cell fixation rate and a cell survival rate are reduced after pancreatic islet cell transplantation.

Therefore, the present invention has been made to solve the above-described problems by using an elastin-like artificial extracellular matrix having excellent biocompatibility, which enables the formation of an environment similar to a pancreatic extracellular matrix. A pharmaceutical composition for treating diabetes of the present invention, which includes a pancreatic islet cell; and an elastin-like artificial extracellular matrix (REP) prepared by repeated fusion of an elastin-like polypeptide and a ligand, may maintain cell viability and activity in a process of isolating and transplanting a pancreatic islet cell, thereby maximizing transplantation success rates.

The present invention provides a pharmaceutical composition for treating diabetes, including: a pancreatic islet cell; and an elastin-like artificial extracellular matrix (REP) prepared through repeated fusion of an elastin-like polypeptide and a ligand.

The pharmaceutical composition for treating diabetes may include a pancreatic islet cell and an elastin-like artificial extracellular matrix (REP) in a form in which the pancreatic islet cell is reacted with the REP.

In this regard, the pharmaceutical composition for treating diabetes may be administered alone, but the present invention is not limited thereto, and the pharmaceutical composition may be administered along with an additional elastin-like artificial extracellular matrix (REP).

The pancreatic islet cell may be isolated from the pancreas of any one individual selected from the group consisting of a human, a mouse, a rat, a pig, a rabbit, a guinea pig, a hamster, a dog, a cat, a cow, and a goat, but the present invention is not limited to the above examples.

A method of isolating pancreatic islet cells from the pancreas of the individual is not particularly limited as long as it is a known method of isolating pancreatic islet cells, which is generally used for transplantation, but pancreatic islet cells may be isolated by, preferably, collagenase digestion.

In the present invention, the elastin-like polypeptide may be an elastin valine-glycine-valine-proline-glycine (VGVPG) polypeptide (SEQ ID NO: 1), and the ligand may be arginine-glycine-aspartate (RGD) (SEQ ID NO: 2).

That is, the elastin-like artificial extracellular matrix (hereinafter, referred to as "REP") of the present invention is prepared through repeated fusion of a VGVPG polypeptide (SEQ ID NO: I) and RGD (SEQ ID NO: 2), and may be preferably TGPG[VGRGD(VGVPG)6]$_n$WPC where n=10, 12, 15, or 20 (SEQ ID NO: 3), more preferably [VGRGD (VGVPG)6]$_n$ where n=10, 12, 15, or 20 (SEQ ID NO: 4).

Figure 1B:
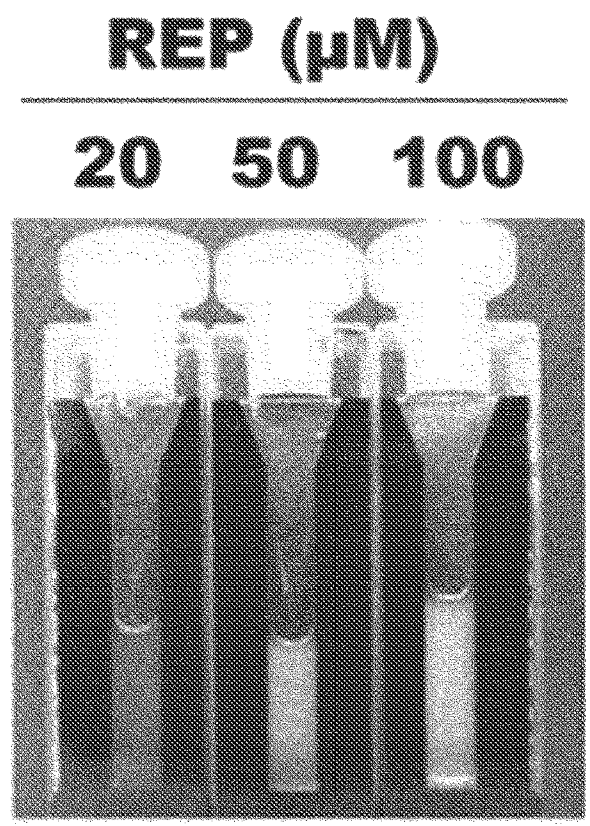
Figure 1C:
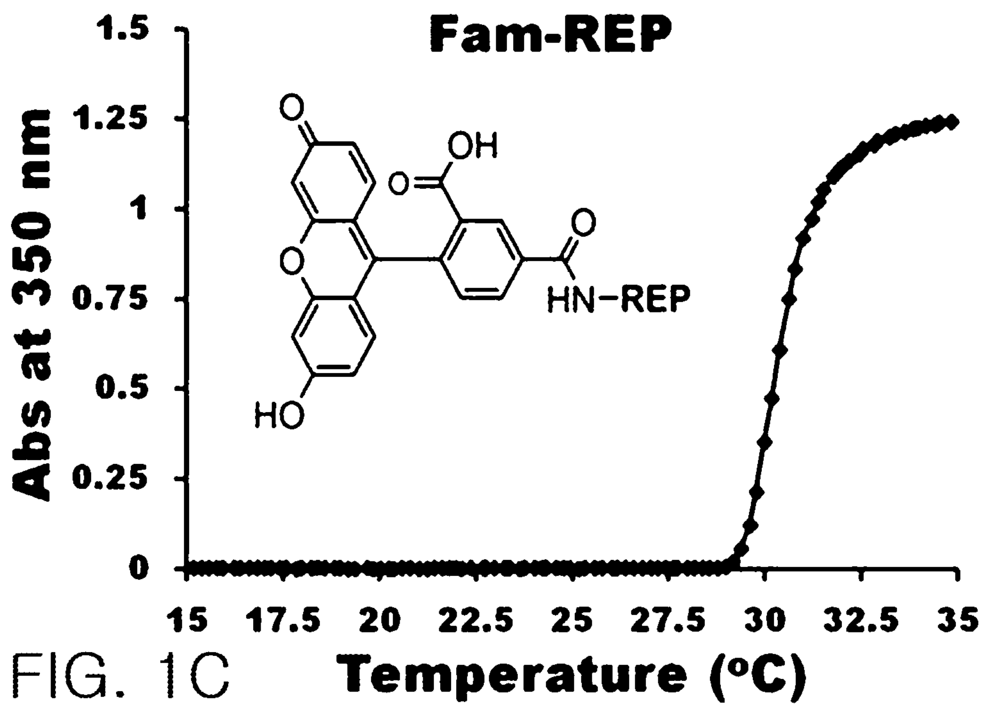
Figure 1D:
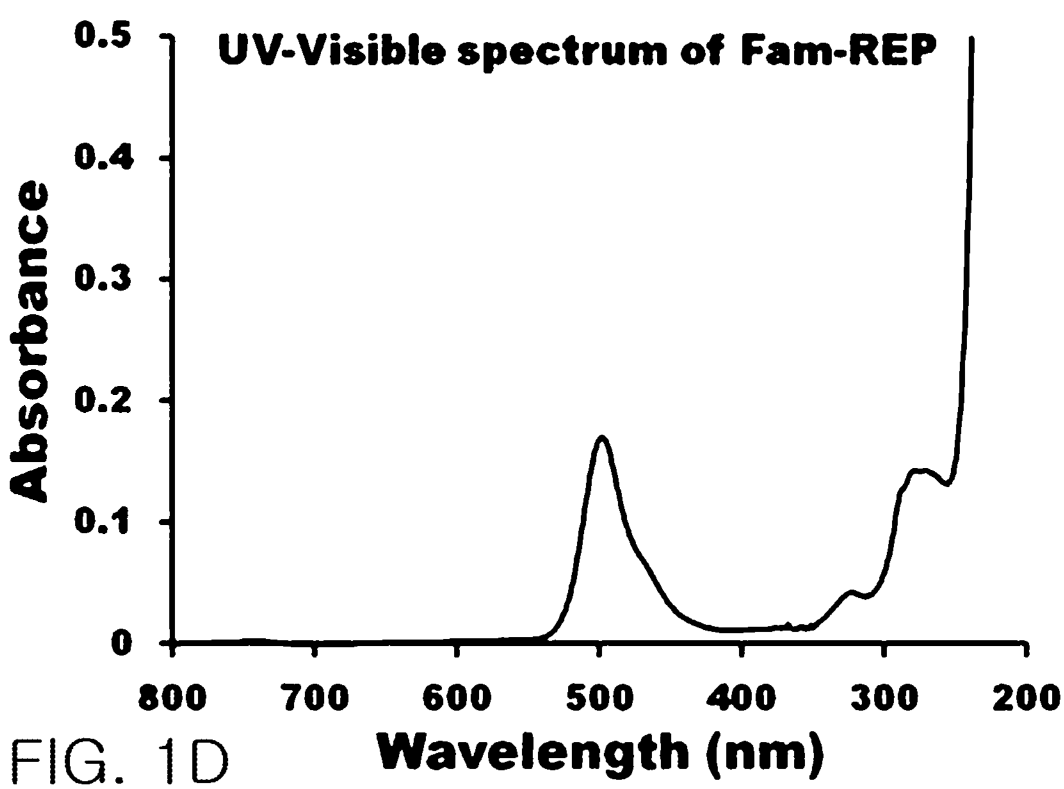

In one embodiment of the present invention, the REP was prepared using a known method (Jeon W B et al., J. Biomed. Mater. Res. A, 97:152, 2011), and Fam-labeled REP (Fam-REP) was prepared and characteristics thereof were examined. As a result of measuring the degree of inverse phase transition of the REP in the presence of DTT, a rapid increase in absorbance was observed at 25° C. or higher (see FIG. 1A), and the coagulation degree of the REP according to concentration was confirmed at 35° C. in a coacervate state (see FIG. 1B). In addition, as illustrated in FIGS. 1C and 1D, it was confirmed that the Fam-REP exhibited an increased absorbance at 30° C. or higher, and a peak appeared around 500 nm. That is, the REP and the Fam-REP may be coagulated in a wound in a coacervate state, due to a specific transition temperature (Tt) thereof that is lower than the body temperature of mice.

The pharmaceutical composition for treating diabetes may include 800 to 2,000 pancreatic islet cells; and 0.5 μM to 10 μM of a REP, preferably, 800 to 1,000 pancreatic islet cells; and 0.5 μM to 1 μM of a REP. When the concentration of the REP and the number of the pancreatic islet cells are smaller than the above-described ranges, a diabetes therapeutic effect may be reduced. Although the concentration of the used REP or the number of used pancreatic islet cells may be greater than the above-described ranges, a sufficient diabetes treatment promotion effect may be obtained even within the above-described ranges. In addition, when the concentration of the REP is 10 μM or more, a superior effect is not exhibited in a concentration-dependent manner, and an additional concentration process is required to realize a concentration of 10 μM or more, and thus it is not suitable in terms of cost efficiency. Even in the case of pancreatic islet cells, it was confirmed that although the cells were administered in a number greater than the above range, an adult stem cell transplantation effect was not significantly increased in a concentration-dependent manner.

In addition, the additional REP administered along with the pharmaceutical composition for treating diabetes of the present invention may be used at the same concentration as that of the REP used in the pharmaceutical composition.

The pharmaceutical composition of the present invention may preferably treat type 1 diabetes, which is insulin-dependent diabetes, but the present invention is not limited thereto.

Figure 2A:
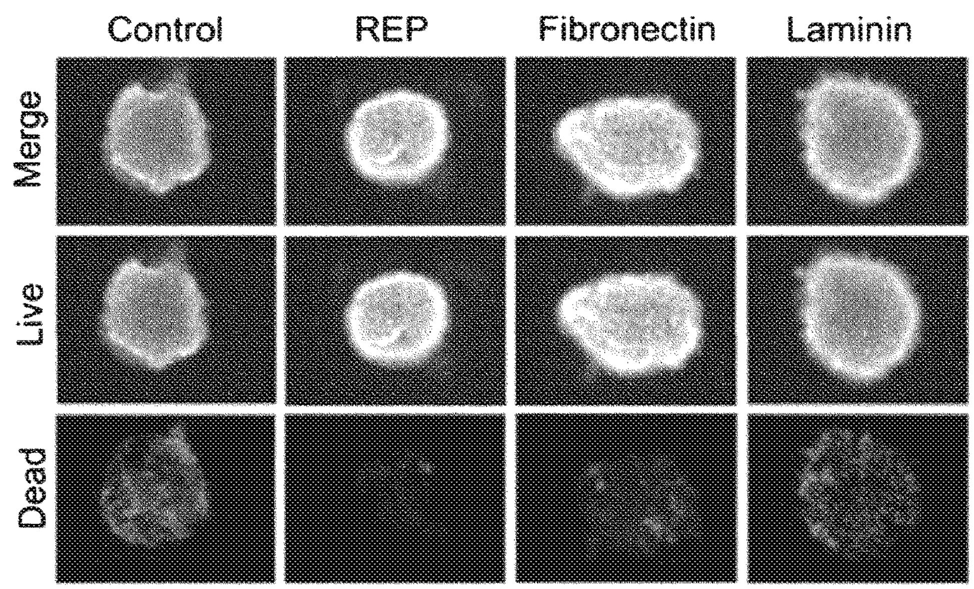
FIG. 2A illustrates fluorescence microscope images showing the cell activity of a pancreatic islet reacted with a REP.

Referring to FIGS. 2A to 2F, it was confirmed that the cell activity and growth rate of pancreatic islet cells reacted with a REP were greater than those of untreated pancreatic islet cells (control) and pancreatic islet cells reacted with fibronectin or laminin (see FIG. 2B), and red fluorescence, which indicates dead cells, was barely observed in the REP-treated pancreatic islet cells, from which it can be seen that the REP increases the activity and growth of pancreatic islet cells (see FIG. 2A). In addition, it can be confirmed that insulin gene expression and insulin secretion due to glucose loading are increased in pancreatic islets reacted with a REP (see FIGS. 2C, 2D, 2E, and 2F).

In addition, as illustrated in FIGS. 3A to 3G, it can be confirmed that the gene and protein expression of PDX-1, BETA2, and Glut2 are increased in REP-treated pancreatic islet cells compared to untreated pancreatic islet cells (see FIGS. 3A, 3B, 3D, and 3F), and it can be confirmed that the gene and protein expression of PCNA and Ki67, which are cell growth markers, are also increased (see FIGS. 3C, 3E, 3F, and 3G). Through this, it was confirmed that pancreatic islet cells transplanted along with a REP after being reacted with the REP increased insulin secretion by increasing insulin gene expression in transplanted patients and maintained the survival rate and activity of the transplanted pancreatic islet cells by promoting cell growth, thereby increasing a transplantation success rate.

Figures 4A, 4B:
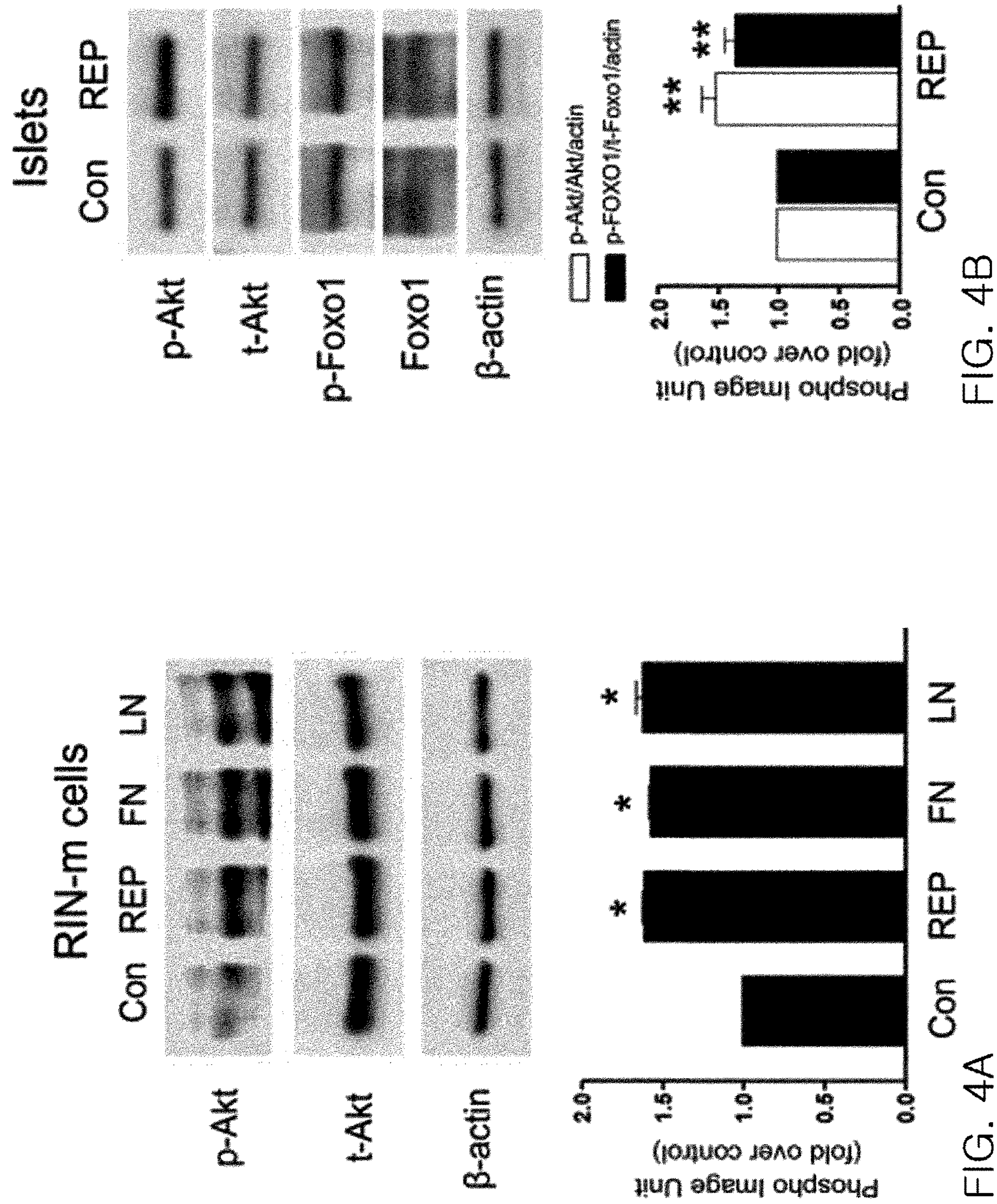

FIGS. 4A to 4E illustrate measurement results of the activity of Akt and foxo1 phosphorylation induced by a REP in pancreatic islet cells, wherein pancreatic beta cells (RIN-m cells), which are insulin-secreting cells, were untreated (positive control), and RIN-m cells were treated with a REP, fibronectin (FN), or laminin (LN), and then the Akt phosphorylation activity of each case was measured (see FIG. 4A), and pancreatic islet cells were untreated or reacted with a REP, and then the Akt and foxo1 phosphorylation activity of each case was measured (see FIG. 4B). As a result, it was confirmed that the Akt phosphorylation activity was increased by a REP, FN, and LN in the pancreatic beta cells (RIN-m cells), and Akt phosphorylation activity levels were mutually similar. In addition, it was confirmed that the Akt and foxo1 phosphorylation was significantly increased in the pancreatic islet cells reacted with a REP compared to the untreated pancreatic islet cells (control). This indicates that REP treatment induces the phosphorylation of Akt and foxo1, which are factors involved in regulating insulin genes, thus promoting insulin secretion. As a result of examining the intracellular migration of Akt and foxo1, the phosphorylation of which had been induced by a REP, through fluorescence staining, it can be confirmed that when Akt phosphorylation is induced by a REP, foxo1 phosphorylation is induced and foxo1, which is expressed in nuclei, is expressed in the cytoplasm (see FIG. 4C). In addition, from an experiment for treatment with wortmannin (Wort), which is an Akt phosphorylation inhibitor, it was confirmed that a REP was bound to PDX-1, which is a transcription factor for regulating insulin genes in nuclei, thereby phosphorylating foxo1, which had inhibited the activity thereof, and inducing the migration of foxo1 into the cytoplasm, resulting in the induction of insulin secretion (see FIGS. 4D and 4E).

Figure 5A:
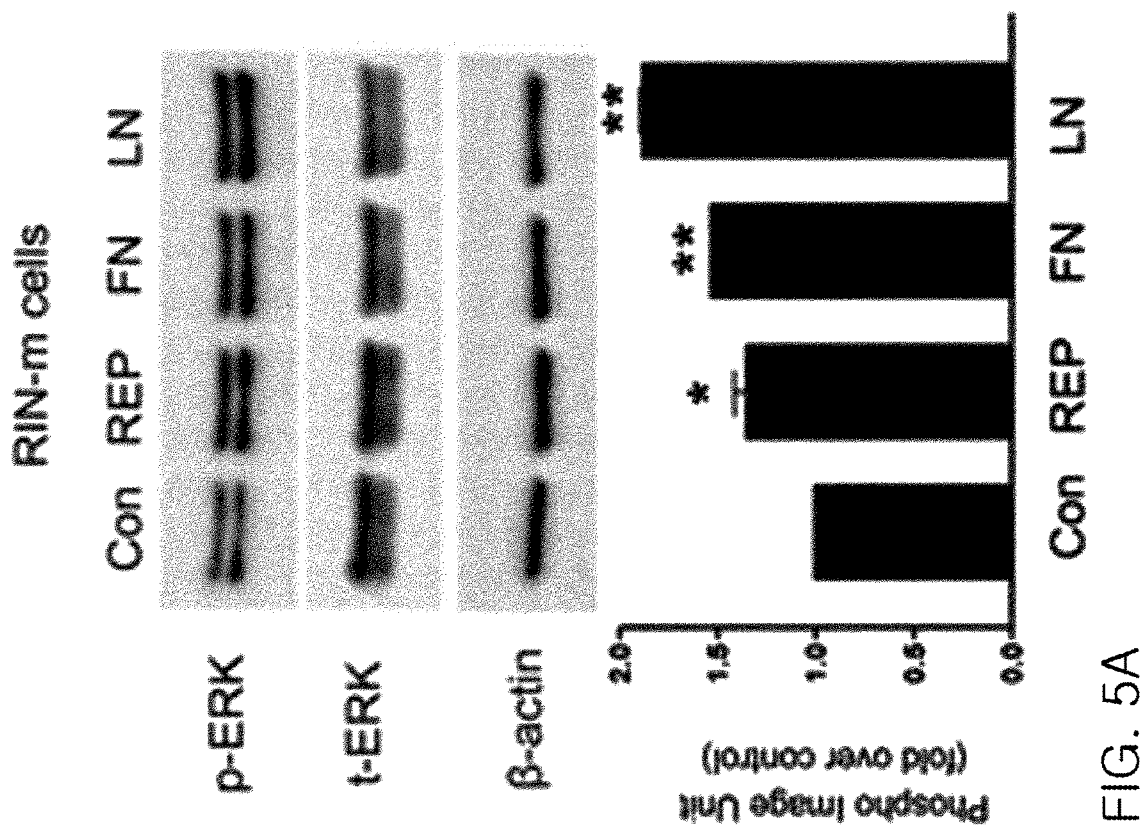
Figures 5B, 5C:
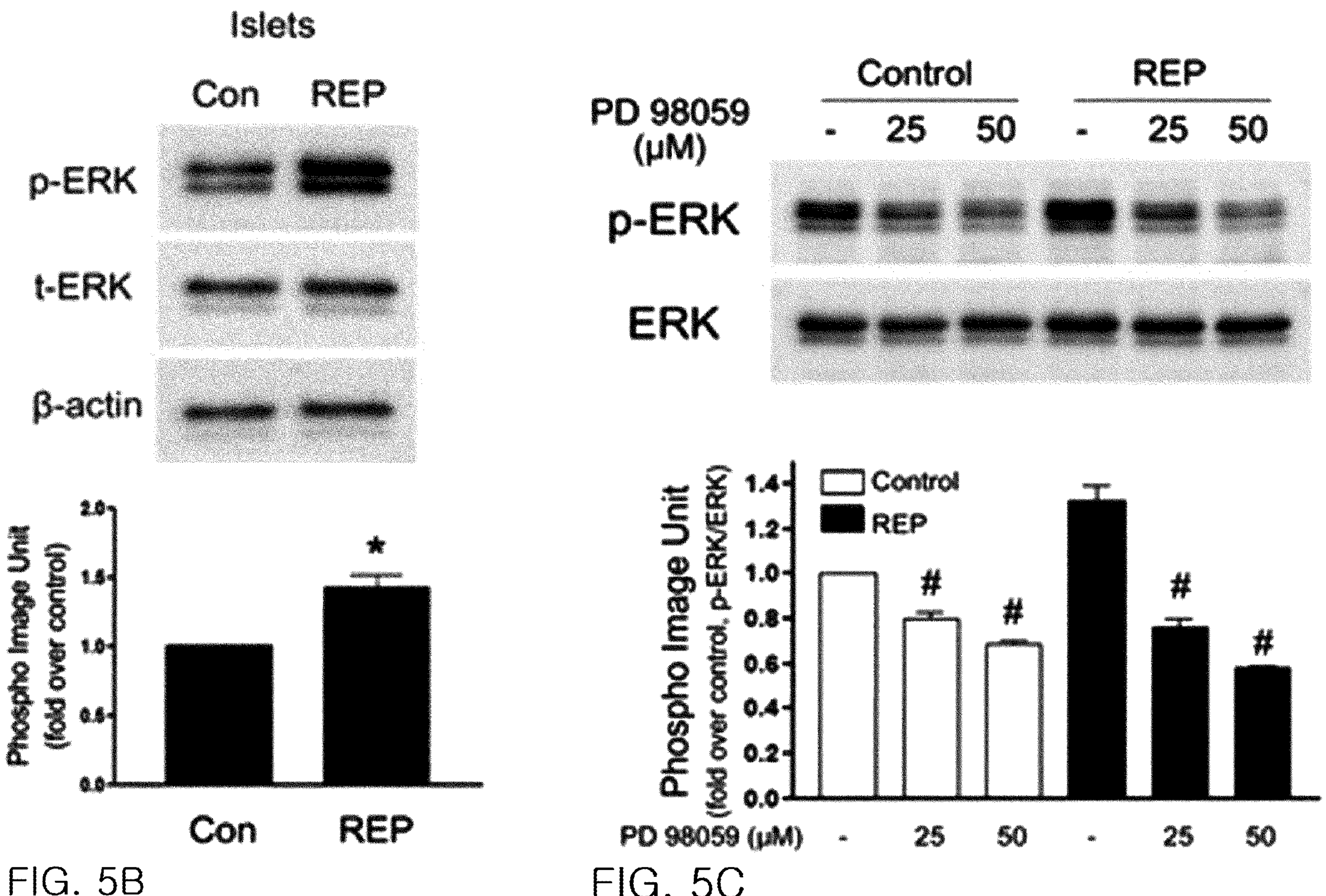
Figure 5E:
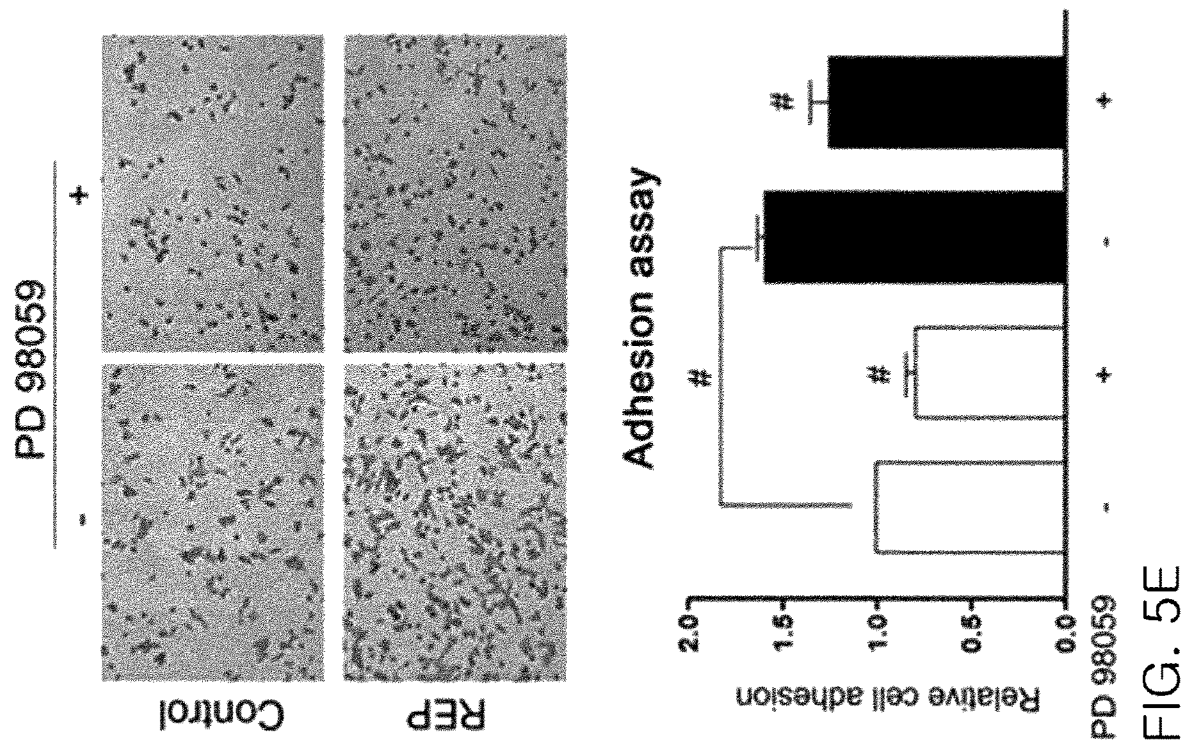
Figure 5D:
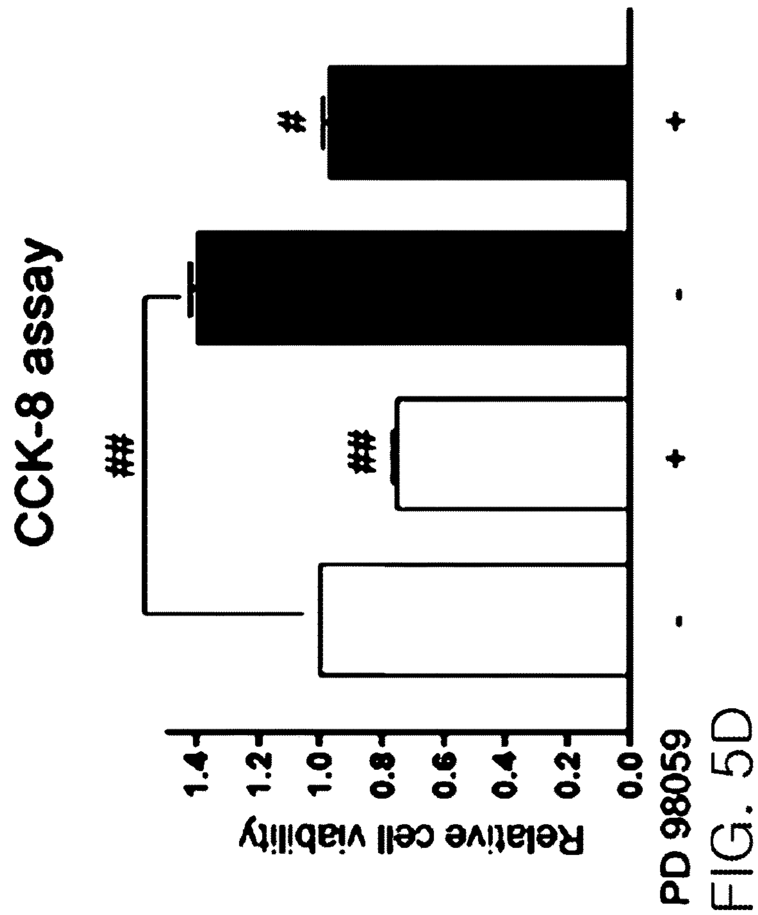

FIGS. 5A to 5E illustrate measurement results of the activity of ERK phosphorylation induced by a REP in pancreatic beta cells and pancreatic islet cells, wherein pancreatic beta cells (RIN-m cells), which are insulin-secreting cells, were untreated, or treated with a REP, fibronectin (FN), or laminin (LN), and then the ERK phosphorylation activity of each case was measured, followed by comparing with untreated pancreatic islet cells or pancreatic islet cells reacted with a REP. As a result, it was confirmed that the pancreatic beta cells treated with a REP, FN, or LN exhibited an increased ERK phosphorylation activity compared to that of the untreated pancreatic beta cells. In addition, it was confirmed that the ERK phosphorylation activity of the pancreatic islet cells reacted with a REP was significantly increased compared to the untreated pancreatic islet cells (see FIGS. 5A and 5B). To examine an increase in cell survival rate and cell adhesion capability according to ERK phosphorylation activated by a REP, an appropriate ERK phosphorylation inhibition concentration was examined by treatment with PD98059, which is an ERK phosphorylation inhibitor, according to concentration, and as a result, it was confirmed that ERK phosphorylation was effectively inhibited at a concentration of 50 μM (see FIG. 5C). FIGS. 5D and 5E illustrate results of verifying that ERK phosphorylation, which had been increased by a REP by treating pancreatic beta cells with PD98059 to inhibit the ERK phosphorylation and then treating the cells with the REP, enhanced a cell survival rate and a cell adhesion ability. It was confirmed that compared to the untreated pancreatic beta cells, the pancreatic beta cells reacted with a REP enhanced the cell survival rate and the cell adhesion ability, and thus maintained the survival rate and activity of the pancreatic beta cells in transplanted patients, thereby enabling a transplantation success rate to increase.

Figure 6A:
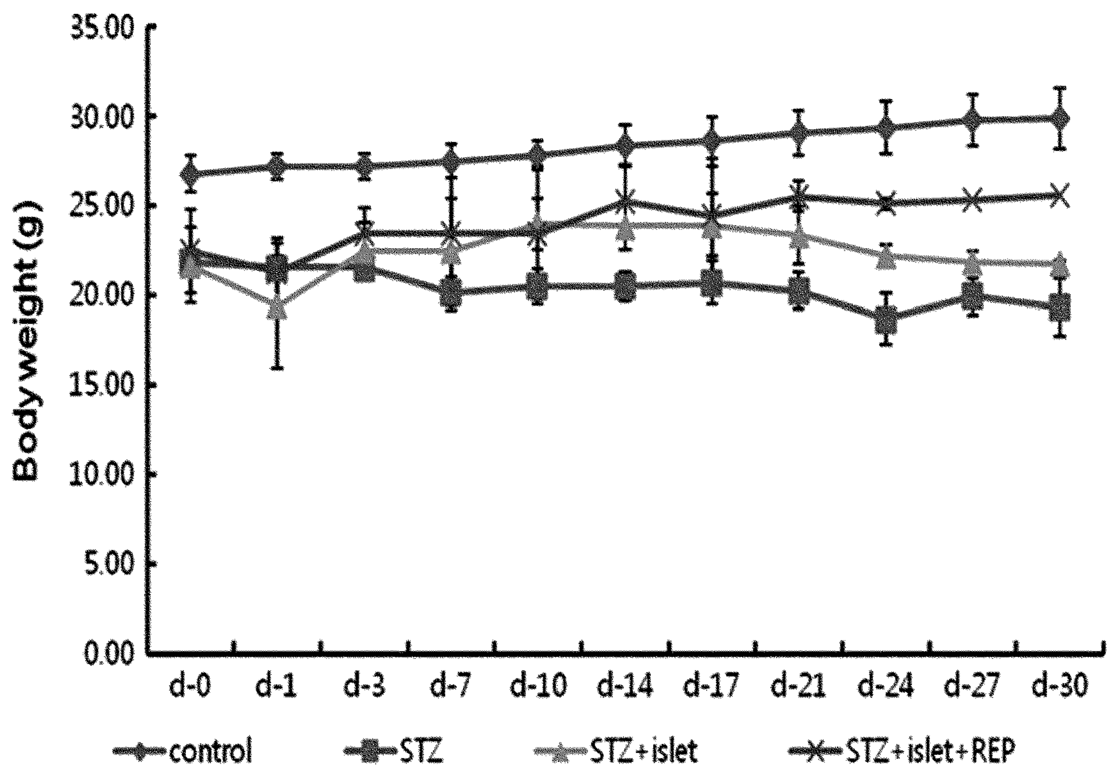
FIGS. 6A and 6B are graphs respectively showing changes in body weight and blood glucose level when pancreatic islet cells were transplanted along with an elastin-like artificial extracellular matrix into streptozotocin-induced diabetic mice.
Figure 6B:
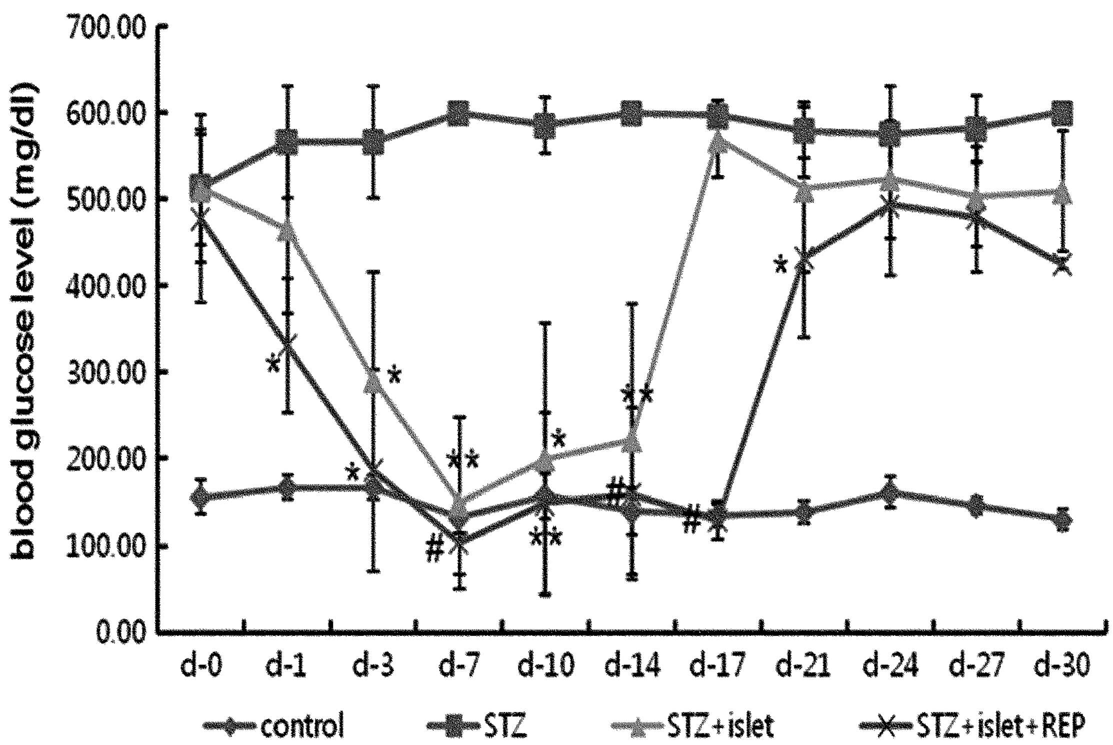

FIGS. 6A and 6B illustrate changes in body weight and blood glucose level when pancreatic islet cells along with a REP were transplanted into streptozotocin-induced diabetic mice, from which it was confirmed that an initial decrease in blood glucose level was more significantly exhibited when pancreatic islet cells were reacted with a REP and then transplanted along with the REP, and the reduced blood glucose level was maintained for a longer period of time. It was also confirmed that a body weight reduced by diabetes induction continued to increase.

Figures 7A, 7B:
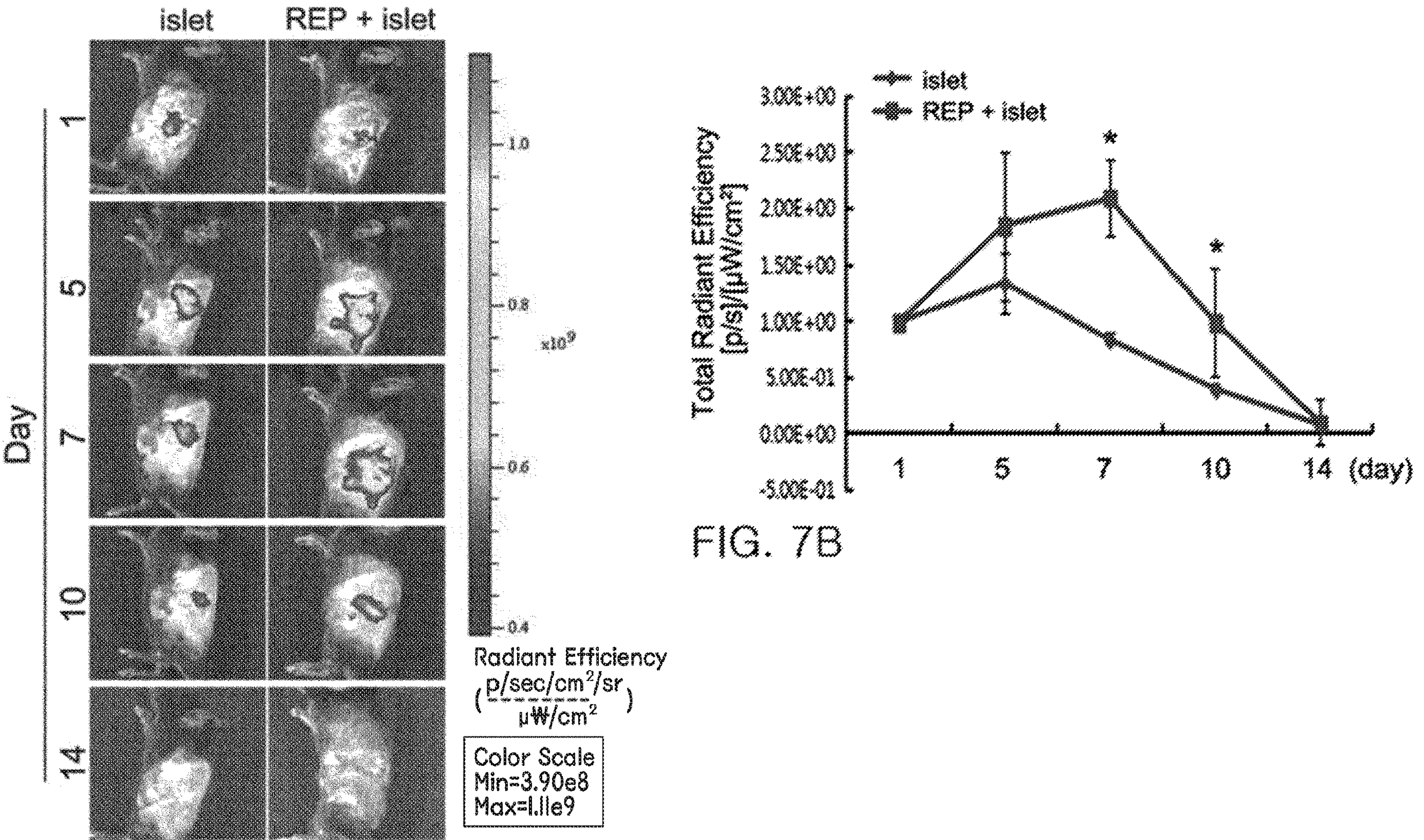
FIG. 7A illustrates fluorescence microscope images showing the real-time survival rate of pancreatic islet cells, which were stained with DiR, after the pancreatic islet cells were transplanted into streptozotocin-induced diabetic mice.
FIG. 7B is a graph showing average radiant efficiency.

Lastly, FIGS. 7A and 7B illustrate the real-time survival rate of transplanted pancreatic islet cells, from which it was confirmed that the survival rate of REP-treated pancreatic islet cells was maintained at a higher level for 7 days after transplantation compared to a case in which only pancreatic islet cells were transplanted into diabetes-induced mice. It was confirmed that although the survival rate of the transplanted pancreatic islet cells was reduced after day 7, the survival rate of the pancreatic islet cells transplanted along with a REP after being treated with the REP was maintained high compared to the case in which only the pancreatic islet cells were transplanted.

Thus, from the results shown in FIGS. 6A, 6B, 7A, and 7B, it was confirmed that the survival rate of the pancreatic islet cells transplanted along with a REP was increased and the blood glucose level thereof was rapidly restored to normal and maintained for a long period of time, and, accordingly, diabetes could be more effectively treated than in the case in which only the pancreatic islet cells were transplanted.

The present invention also provides a method of treating diabetes using the pharmaceutical composition for treating diabetes.

Specifically, the present invention also provides a method of preventing or treating diabetes, including administering, to an individual in need of the treatment of diabetes, a pancreatic islet cell; and a REP prepared through repeated fusion of an elastin-like polypeptide and a ligand.

The term "individual" as used herein refers to an animal, which is a subject of treatment, observation, or an experiment, preferably a mammal, and most preferably a human. Preferably, the individual experiences or exhibits one or more symptoms of the disease or disorder to be treated and/or prevented.

The terms "treating" and "treatment" as used herein are intended to include the management and care of an individual or patient (preferably a mammal, more preferably a human) for the purpose of eliminating a disease, a condition, or a disorder, unless otherwise stated herein. The terms "treating" and "treatment" as used herein are intended to include administering the pharmaceutical composition described herein to (a) alleviate one or more symptoms or complications of a disease, a condition, or a disorder; (b) prevent the onset of one or more symptoms or complications of a disease, a condition or a disorder; and/or (c) eliminate one or more symptoms or complications of a disease, a condition or a disorder.

The terms “preventing” and “prevention” as used herein are intended to include, unless otherwise stated herein, (a) reducing the frequency of one or more symptoms; (b) reducing the severity of one or more symptoms; (c) delaying, slowing, or avoiding the onset of one or more additional symptoms; and/or (d) delaying, slowing, or avoiding the progression of a disease, a condition, or a disorder into a terminal or more severe form.

It will be appreciated by those of ordinary skill in the art that when the present invention relates to a prevention method, an individual in need of this (i.e., an individual in need of prevention) includes an arbitrary individual or patient (preferably a mammal, more preferably a human) that experiences or exhibits one or more symptoms of a disorder, disease or condition to be prevented. In addition, the individual may be an individual (preferably a mammal, more preferably a human) that has never exhibited any symptom of a disorder, disease or condition to be prevented, but is considered to be at risk of developing the disorder, the disease, or the condition by a physician, a clinician, or other medical practitioners. For example, an individual may be considered to be at risk of developing a disorder, disease or condition due to family history, predisposition, or a coexisting disorder (comorbidity) (thus in need of prevention or preventative treatment).

The pharmaceutical composition for treating diabetes of the present invention may be formulated using a method known in the pharmaceutical field, and may be formulated into a variety of general pharmaceutical preparations by mixing with a structure itself or a pharmaceutically acceptable carrier, an excipient, or the like. A dosage of the pharmaceutical composition of the present invention is not particularly limited, but a suitable dose thereof varies according to the condition and body weight of patients, the severity of diseases or conditions, drug form, and administration period, and may be appropriately selected by those of ordinary skill in the art. For a desired effect, the pharmaceutical composition of the present invention may be administered in an amount of 0.5 μM to 10 μM, preferably 0.5 μM to 1 μM.

The present invention also relates to a use of a pancreatic islet cell; and a REP prepared through repeated fusion of an elastin-like polypeptide and a ligand, for the preparation of a cellular therapeutic agent for treating diabetes.

The term “cellular therapeutic agent” as used herein refers to a drug used for the purpose of treatment, diagnosis, and prevention, which contains cells or tissues prepared by isolation from a human, culturing, and specific manipulation (US FDA regulations), and refers to a pharmaceutical product used for the purpose of treatment, diagnosis, and prevention, obtained through a series of actions, including growing and screening living autologous, allogenic, or xenogenic cells in vitro in order to restore the function of the cells or tissues or changing the biological characteristics of cells by any other methods.

Hereinafter, the present invention will be described in further detail with reference to the following examples. It will become apparent to those of ordinary skill in the art that these examples are provided only for illustrative purposes and are not intended to limit the scope of the present invention.

EXAMPLES

Example 1

Preparation of Elastin-Like Artificial Extracellular Matrix (REP) and Verification of Characteristics Thereof The purification of a REP and the verification of a specific transition temperature (Tt) thereof were performed using the same method as that described in the paper Stimulation of fibroblasts and neuroblasts on a biomimetic extracellular matrix consisting of tandem repeats of the elastic VGVPG domain (SEQ ID NO: 1) and RGD motif (SEQ ID NO: 2)” (Jeon WB et al., J. Biomed. Mater. Res. A, 97:152, 2011).

To conjugate 5-carboxyfluorescein (Fam) to the N-terminal of the prepared REP, 5 μmol of 5-carboxyfluorescein N-succinimidyl ester (Sigma, USA) was dissolved in 580 μl of DMSO, and then 20 ml of PBS containing 0.97 mol of the REP was added thereto. The resulting mixture was allowed to react at room temperature for 3 hours, thereby completing the preparation of a Fam-labeled REP (Fam-REP). The Fam-REP was purified by inverse phase transition. The degree of labeling was measured using an AnaTag™ protein labeling kit (AnaSpec, USA) according to the protocol included in the kit.

The degree of inverse phase transition of the REP was measured in the presence of DTT according to changes in REP concentration (20 μM, 50 μM, and 100 μM) and temperature. The temperature was increased at a rate of 1° C./min. As a result, a rapid increase in absorbance was observed at 25° C. or higher (see FIG. 1A), and REP coagulation was measured at 35° C. in a coacervate state according to concentration (see FIG. 1B).

In addition, as a result of measuring the degree of inverse phase transition of the Fam-REP in the presence of DTT, absorbance was increased at 30° C. or higher (see FIG. 1C), and as a result of measuring a change in absorbance according to the wavelength of the Fam-REP (see FIG. 1D), it was confirmed that a peak appeared around 500 nm.

Example 2

Isolation of Pancreatic Islet Cells and Treatment with Elastin-Like Artificial Extracellular Matrix Pancreatic islet cells were isolated from the pancreas of 10-week-old white mice by collagenase digestion as follows.

Collagenase type 5 was dissolved at a concentration of 1 mg/ml in a Hank’s balanced salt solution (HBSS) and then kept in a cold state. The experimental animals were anesthetized and the abdomen of each mouse was incised, and then collagenase was injected into the pancreatic duct through the common bile duct. The pancreas was isolated and allowed to react in a thermostat bath at 37° C. for 10 minutes to digest the pancreas. The digested pancreas was washed with HBSS and only pancreatic islet cells were isolated therefrom while being observed using a microscope. The isolated pancreatic islet cells were cultured in a RPMI-1640 medium supplemented with 10% fetal bovine serum (FBS) and 100 U/ml penicillin and 100 μg/ml of streptomycin for 16 hours. 1,000 pancreatic islet cells were placed in 1 ml of 1 μM of the REP and allowed to react at 4° C. for 1 hour while being stirred to be used for transplantation.

Example 3

1. Measurement of Cell Activity and Growth

To examine the effect of REP treatment on the cell activity of pancreatic islet cells, pancreatic islet cells were reacted with a REP solution, and then cultured on a REP-coated plate.

For cell activity measurement, a LIVE/DEAD reagent purchased from Molecular Probes was used. An artificial pancreatic islet cultured on a plate was washed three times with phosphate buffered saline (PBS), treated with a LIVE/DEAD reagent containing 2 μM of calcein AM and 4 μM of EthD-1, and then allowed to react at room temperature for 30 minutes, followed by observation using a fluorescence microscope. Cell growth was measured using Cell Counting Kit-8 (CCK-8). Pancreatic islet cells were reacted with RGD (SEQ ID NO: 2)-ELP, allowed to react on a 96-well plate coated with 1 μM of a REP for 24 hours, treated with 10 μL of a CCK-8 solution, and then allowed to react at 37° C. for 3 hours, followed by analysis using a microplate reader at OD 450 nm.

Figure 2B:
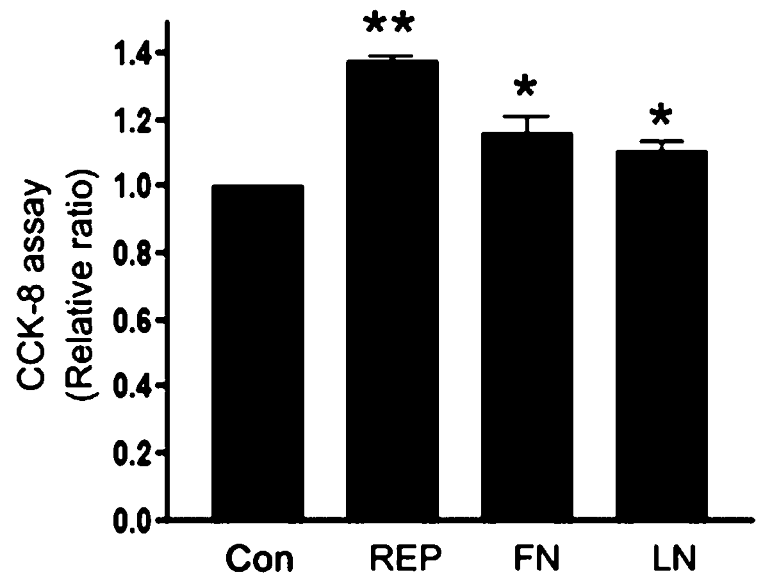
FIG. 2B is a graph showing the growth rate of pancreatic islet cells reacted with a REP solution through a CCK-8 assay.

As a result, as illustrated in FIG. 2A, cell activity was higher (calcein AM, green fluorescence, live cells were stained) in the case of REP treatment compared to treatment with other types of extracellular matrices such as fibronectin or laminin, and dead cells were barely observed (EthD-1, red fluorescence, and dead cells were stained). In addition, as illustrated in FIG. 2B, through CCK-8 assay, it was confirmed that the growth rate of the pancreatic islet cells reacted with the REP solution was much higher than in the case of fibronectin or laminin.

2. Measurement of Insulin Gene Expression and Insulin Secretory Capacity

To examine the effect of REP treatment on insulin gene expression and insulin secretory capacity, pancreatic islet cells were reacted with a REP solution and cultured on a REP-coated plate, and then insulin gene expression and insulin secretory capacity were measured.

To verify gene expression, quantitative real time PCR (qRT-PCT) was used. To isolate RNA from the artificial pancreatic islet formed by RGD (SEQ ID NO: 2)-ELP, a TRIzol reagent manufactured by Invitrogen was used, and cDNA was synthesized using a high-capacity cDNA reverse transcription kit manufactured by Applied Biosystems. The qRT-PCR was performed using a SYBR Green PCR master mix kit, and the PCR was performed at 50° C. for 2 minutes, at 95° C. for 10 minutes, at 95° C. for 15 seconds, and at 60° C. for 1 minute, and this cycle of PCR was repeated 40 times. Changes in gene expression of insulin-1 and insulin-2 were analyzed by qRT-PCR.

To verify insulin secretory capacity, REP-treated pancreatic islet cells were maintained in a Krebs Ringer bicarbonate buffer (KRBB) solution containing 3 mM glucose and 2% FBS in a thermo-hygrostat at 37° C. for 5 hours. Subsequently, the resulting cells were treated with 3 mM glucose or 16.7 mM glucose, and then the supernatant was collected, and 10 μl of the supernatant was analyzed using a rat ultrasensitive insulin ELISA kit manufactured by ALPCO according to the manufacturer's manual.

Figure 2C:
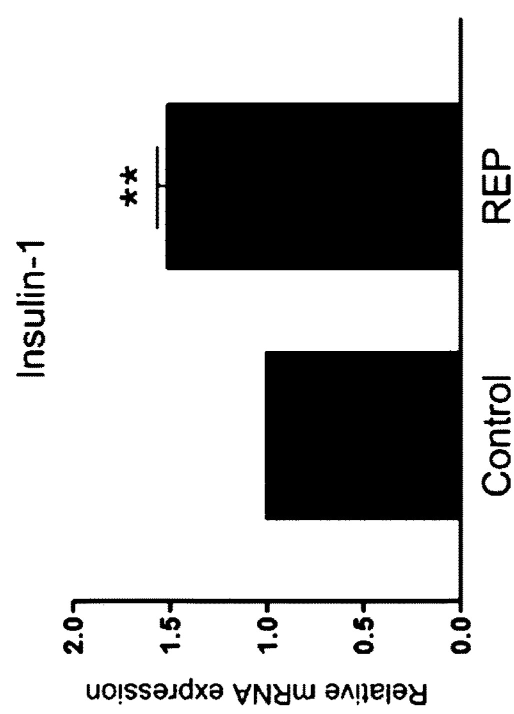
FIGS. 2C and 2D are graphs showing the insulin gene expression of a pancreatic islet reacted with a REP by quantitative real time PCR.
Figure 2D:
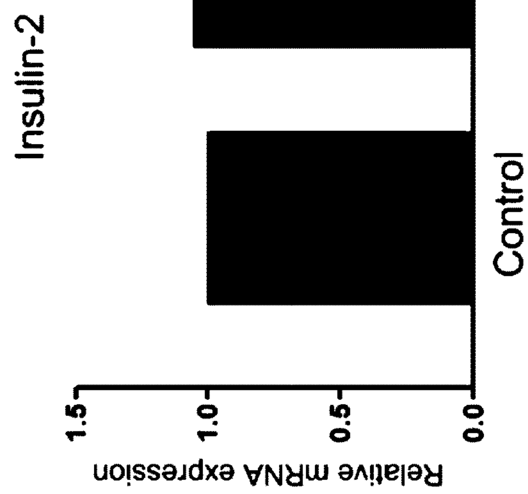
Figure 2E:
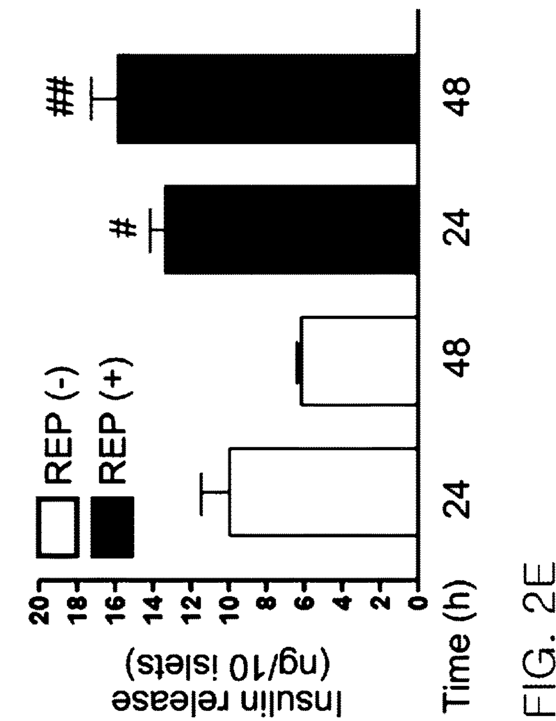
FIGS. 2E and 2F are graphs showing insulin release and insulin secretion according to glucose loading using an insulin ELISA kit.
Figure 2F:
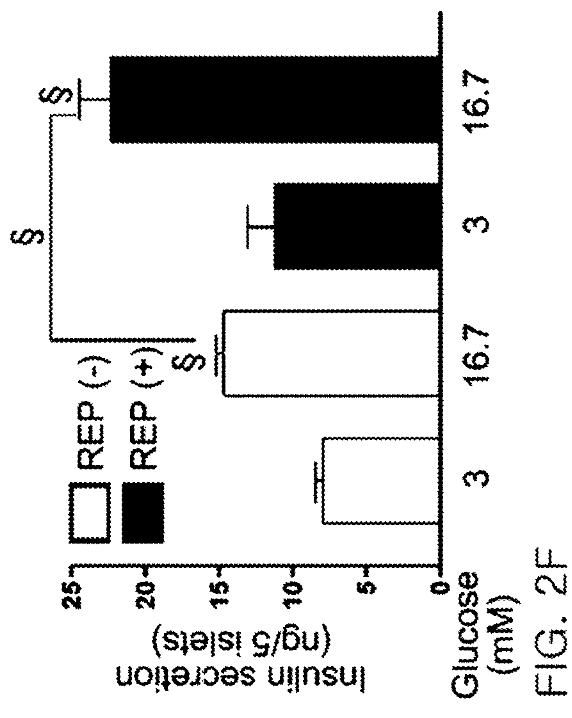
Figure 3A:
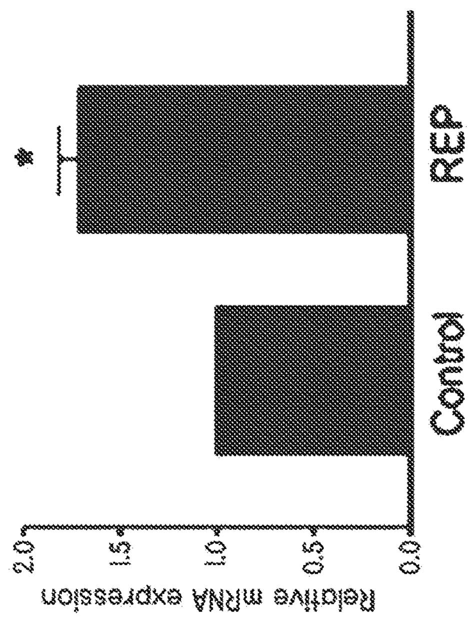
Figure 3B:
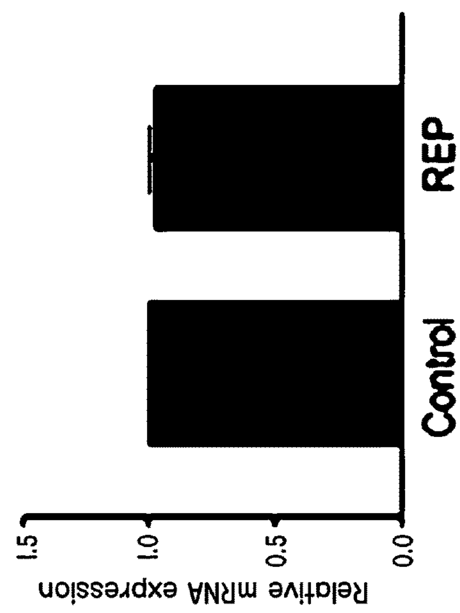
Figure 3C:
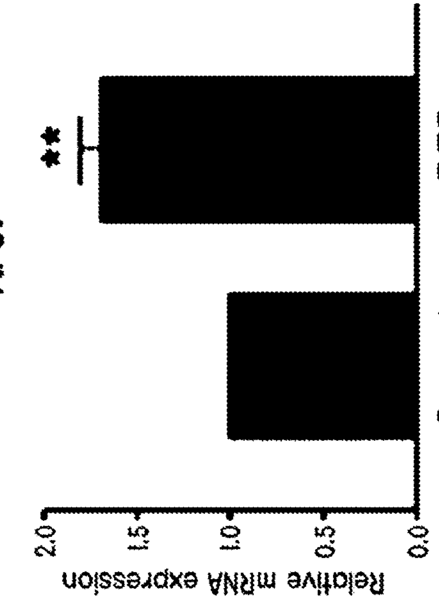
Figure 3D:
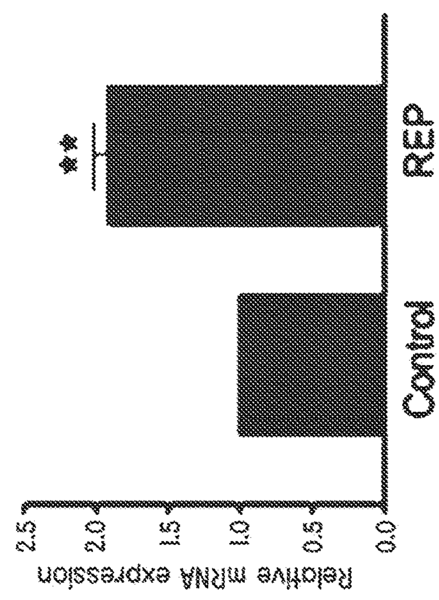

As illustrated in FIGS. 2C and 2D, it was confirmed that the gene expression of insulin-1 and insulin-2 was increased compared to the control. In addition, as illustrated in FIGS. 2E and 2F, it was confirmed that insulin secretion was increased over time by REP treatment, and insulin secretory capacity according to glucose loading (treated with 16.7 mM D-glucose) was also increased.

Example 4

Measurement of Expression of Transcriptional Activator that Regulate Insulin Gene Expression and Cell Growth Marker To verify the effect of REP treatment on insulin secretion and cell growth, pancreatic islet cells were reacted with a REP solution and cultured on a REP-coated plate, and then the gene and protein expression of PDX-1, BETA2, and Glut2, which are transcriptional activators that regulate the insulin gene expression of pancreatic islet cells, and the gene and protein expression of PCNA and Ki67, which are cell growth markers, were measured as follows.

To verify gene expression, quantitative real time PCR (qRT-PCR) was used as described in Example 3 above.

In addition, western blot analysis was used to verify protein expression. Cell lysates were extracted from REP-treated pancreatic islet cells by using a RIPA buffer containing a protease inhibitor and a phosphatase inhibitor. The cell lysates were loaded onto a SDS-PAGE gel, and then transferred to a PVDF membrane, and changes in protein expression were examined using an anti-PDX-1 antibody, an anti-BETA2 antibody, an anti-Glut2 antibody, an anti-PCNA antibody, and an anti-PCNA antibody. Ki67 protein expression was measured using a Ki67 ELISA kit manufactured by MyBioSource according to the manufacturer's manual.

As a result, as illustrated in FIGS. 3A, 3B, 3D, and 3F, it was confirmed that the gene and protein expression of PDX-1, BETA2, and Glut2 was increased in the REP-treated pancreatic islet cells compared to untreated pancreatic islet cells. In addition, as illustrated in FIGS. 3C, 3E, 3F, and 3G, it was confirmed that the gene and protein expression of PCNA and Ki67, which are cell growth markers, was also increased. From the above results, it can be expected that pancreatic islet cells transplanted along with a REP after being reacted with the REP increases insulin secretion by increasing insulin gene expression in a transplanted patient, and promotes cell growth, and thus the survival rate and activity of the transplanted pancreatic islet cells were maintained, thereby significantly increasing a transplantation success rate.

Example 5

Akt and Foxo1 Phosphorylation Induced by REP in Pancreatic Islet Cells

To verify the effect of REP treatment on insulin secretion of pancreatic islet cells, pancreatic islet cells were reacted with a REP solution and cultured on a REP-coated pate, and then the phosphorylation activity of Akt and foxo1, which regulate factors involved in insulin gene regulation of pancreatic islet cells, was measured by western blotting using an anti-p-Akt-antibody and an anti-p-foxo1 antibody. The intracellular migration of the phosphorylated Akt and foxo-1 was measured by fluorescent staining.

Pancreatic islet cells reacted with a REP were fixed in a 4% paraformaldehyde solution for 24 hours, and then cut to a thickness of 4 μm using a cryomicrotome, and the section was attached to a slide. The section attached to a slide was allowed to react in a blocking buffer for 1 hour, allowed to react with p-Akt and p-foxo1 antibodies (Abcam) for 48 hours, washed with PBS, allowed to react with AlexaFluor 488 anti-rabbit IgG secondary antibodies (Invitrogen) for 2 hours, and then washed with PBS. The nuclei were stained with DAPI and then observed using a fluorescence microscope.

RIN-m cells, which are pancreatic beta cells that secrete insulin, were untreated (positive control), or treated with a REP, fibronectin (FN), or laminin (LN), and then Akt phosphorylation activity of each case was measured, followed by comparing with pancreatic islet cells which were untreated or reacted with a REP (see FIGS. 4A and 4B). As a result, it was confirmed that the Akt phosphorylation activity of the pancreatic beta cells (RIN-m cells) was increased by a REP, FN, or LN, and the phosphorylation activities of these cases are mutually similar. In addition, it was confirmed that the Akt and foxo1 phosphorylation was significantly increased in the pancreatic islet cells reacted with a REP compared to the untreated pancreatic islet cells (control).

Figure 4C:
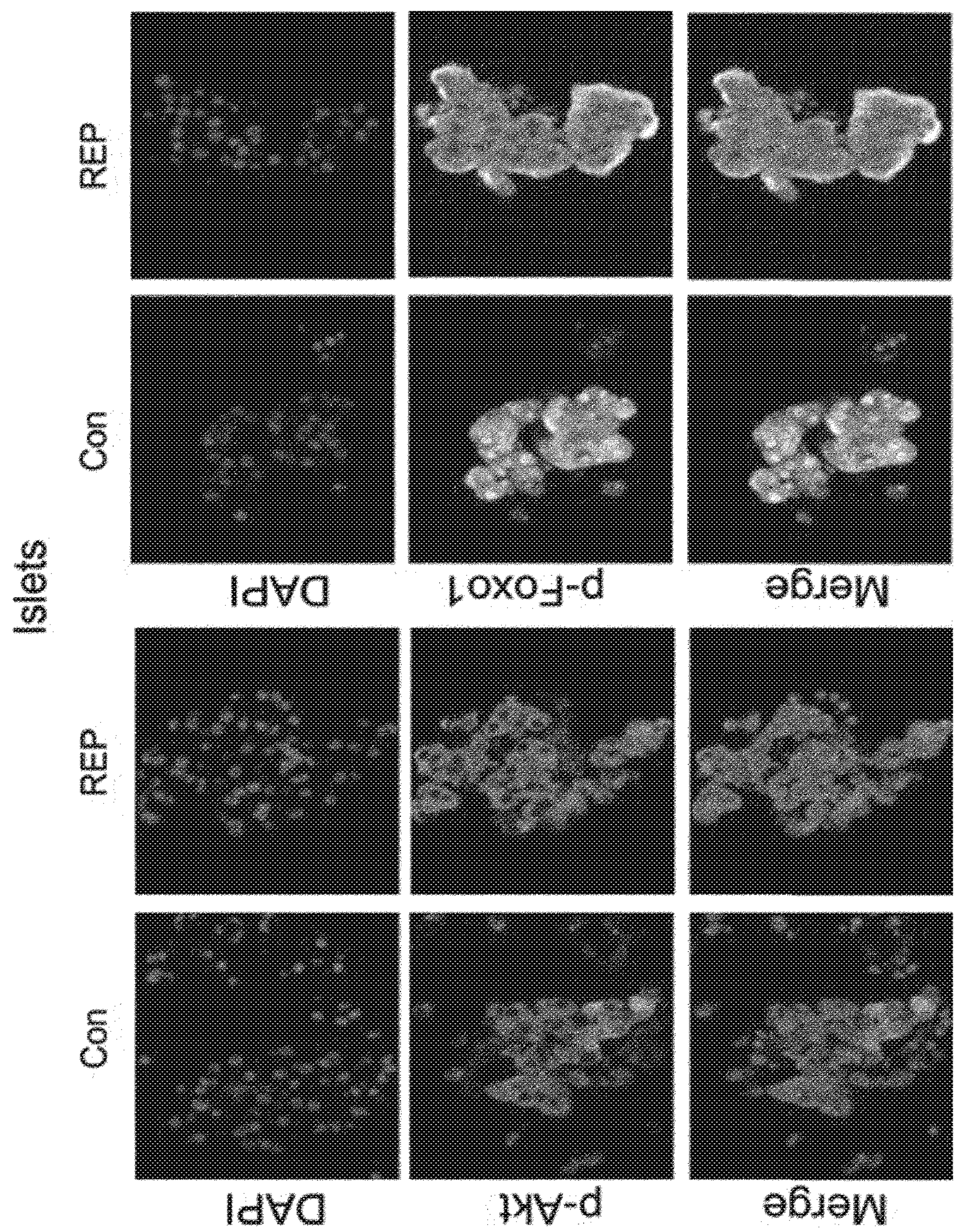
Figure 4D:
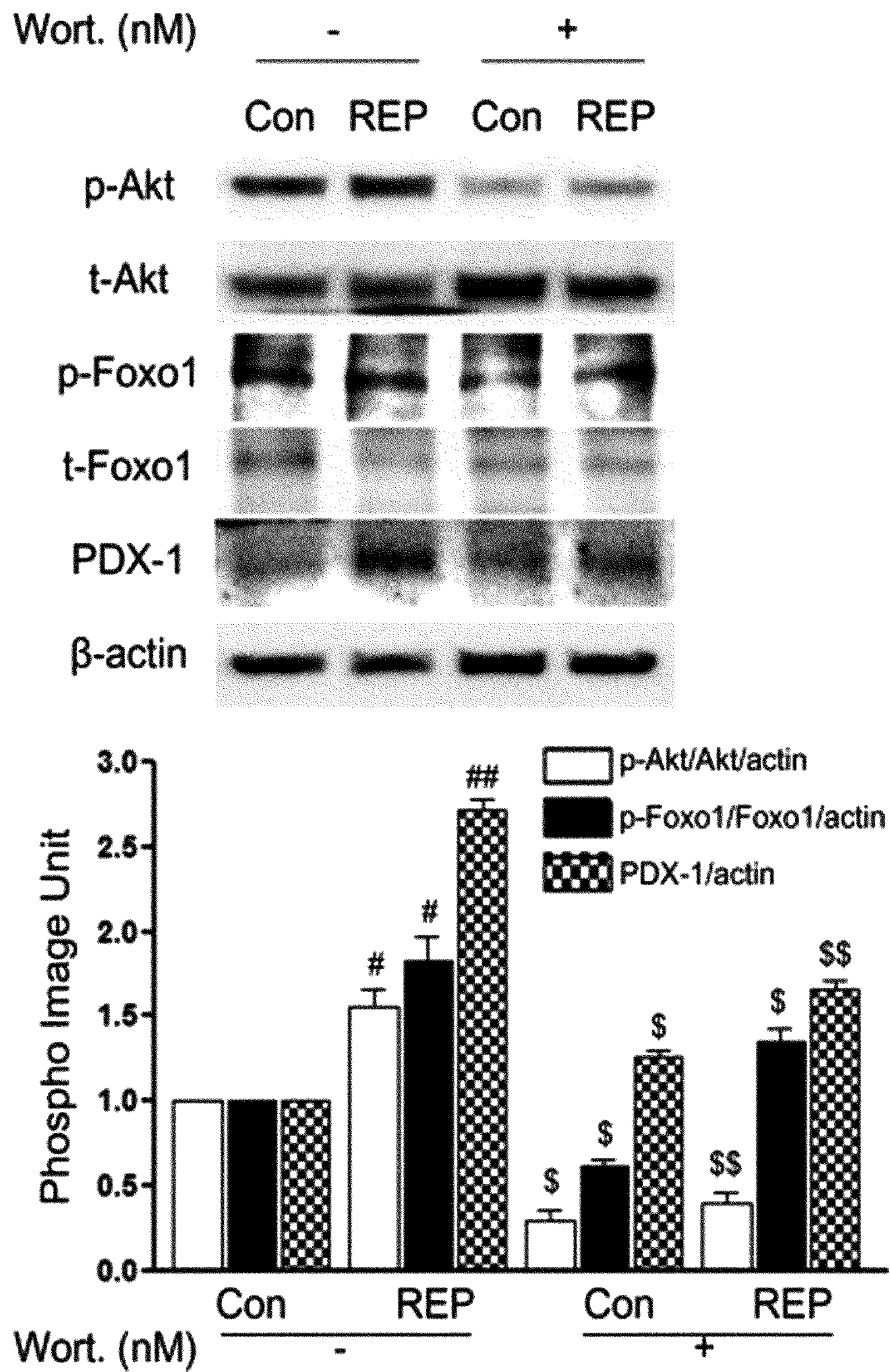
Figure 4E:
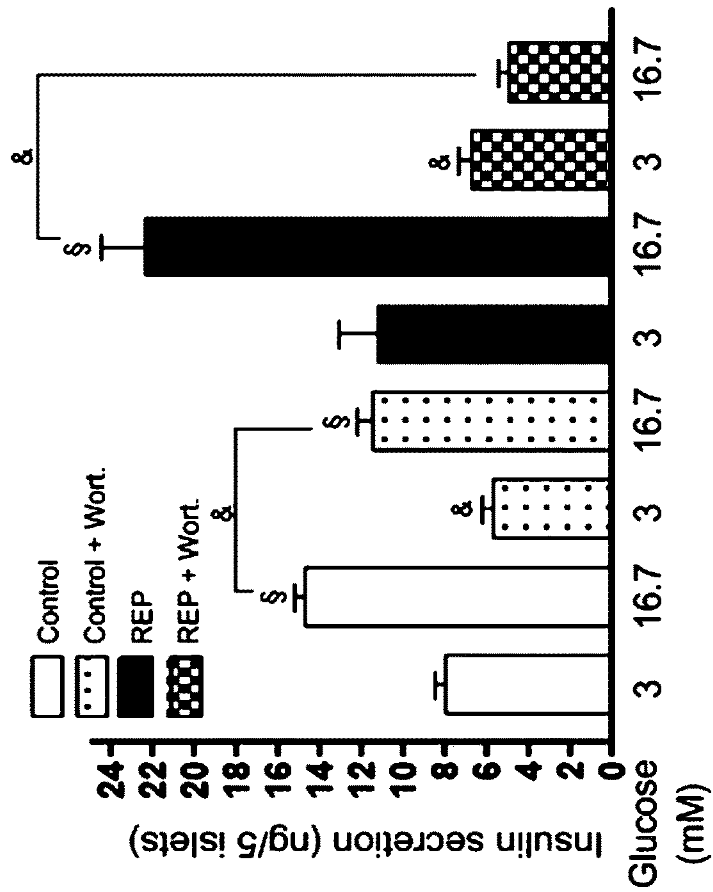

As a result of examining the intracellular migration of Akt and foxo1, which had been phosphorylated by the REP in pancreatic islet cells, it was confirmed that the expression of the phosphorylated Akt in nuclei was increased by REP treatment, and the expression of the phosphorylated foxo1 in the cytoplasm was increased (see FIG. 4C). To confirm that the phosphorylation of Akt caused by the REP was closely correlated with the regulation of insulin expression, Akt and foxo1 phosphorylation, PDX-1 expression, and insulin secretion according to glucose loading were measured after treatment with wortmannin, which is an Akt phosphorylation inhibitor. As a result, it was confirmed that due to treatment with wortmannin, the Akt and foxo1 phosphorylation and the PDX-1 expression, which had been increased by the REP, were reduced and the insulin secretory capacity increased according to glucose loading was also decreased (see FIGS. 4D and 4E). This indicates that the REP treatment promotes insulin secretion by inducing the expression of PDX-1, which is a transcriptional activator involved in insulin gene regulation, through the phosphorylation of Akt and foxo1.

Example 6

ERK Phosphorylation Induced by REP in Pancreatic Beta Cells and Pancreatic Islet Cells To examine the effect of REP treatment on the phosphorylation of ERK, which is a signaling pathway that increases the growth and viability of pancreatic islet cells, pancreatic islet cells were treated with a REP solution and cultured on a REP-coated plate, and then the phosphorylation activity of ERK was examined by western blotting through protein changes using an anti-p-ERK-antibody.

Pancreatic beta cells (RIN-m cells), which are insulin-secreting cells, were untreated (positive control), or treated with a REP, fibronectin (FN), or laminin (LN), and then the ERK phosphorylation activity of each case was measured, and compared with pancreatic islet cells which were untreated or reacted with a REP. As a result, it was confirmed that the pancreatic beta cells treated with a REP, FN, or LN exhibited an increased ERK phosphorylation activity compared to that of the untreated pancreatic beta cells. It was also confirmed that the ERK phosphorylation activity of the REP-treated pancreatic islet cells was significantly increased compared to the untreated pancreatic islet cells (see FIGS. 5A and 5B). To find an appropriate concentration of PD98059, which is an ERK phosphorylation inhibitor, the REP treatment was performed according to concentration, and it was confirmed that treatment with the REP at a concentration of 50 μM effectively inhibited the phosphorylation of ERK (see FIG. 5C).

Lastly, pancreatic beta cells were treated with PD98059 to inhibit the phosphorylation of ERK, and then treated again with a REP, and it was examined whether the ERK phosphorylation, which had been increased by the REP, affected a cell survival rate and a cell adhesion ability. As a result, as illustrated in FIGS. 5D and 5E, it was confirmed that compared to the untreated pancreatic islet cells, the REP-treated pancreatic islet cells had an enhanced cell survival rate and an enhanced cell adhesion ability, and thus the survival rate and activity of the pancreatic islet cells were maintained in transplanted patients, thereby increasing a transplantation success rate.

Example 7

1. Construct of Diabetes Experimental Animal Model 10-week-old C57BL6 mice were intraperitoneally administered 250 mg/kg of streptozotocin once. 4 to 5 days after streptozotocin administration, blood glucose levels were measured after collecting blood from the tail of each mouse, and mice having a blood glucose level exceeding 360 mg/dL were classified as having diabetes and used for a transplantation experiment.

2. DiR Fluorescent Staining and Transplantation of Pancreatic Islet Cells

Pancreatic islet cells to be used for transplantation were allowed to react with 320 μg/mL of a DiR buffer for 30 minutes, and then centrifuged at 4° C. and 1,000 rpm for 3 minutes to collect a cell pellet. The stained cells were washed twice with PBS and collected in a PE tube for transplantation. Diabetes-induced mice were anesthetized, and then pancreatic islet cells reacted with the REP prepared according to Example 2 and an additional REP, which had not been reacted with pancreatic islet cells, were transplanted into a lower part of the renal capsule, and blood glucose levels and body weight were measured on a daily basis.

3. Changes in Blood Glucose Level and Body Weight of Diabetes-Induced Mice with Pancreatic Islet Transplanted Thereinto In the case of mice with diabetes induced by treatment with streptozotocin, the blood glucose level was confirmed to be maintained at 500 mg/dl to 600 mg/dl, and it was also confirmed that body weight continued to decrease. As illustrated in FIGS. 6A and 6B, it was confirmed that when only pancreatic islet cells are transplanted into the diabetes-induced mice, the blood glucose level was decreased, and reduced close to normal on day 7. In contrast, it was confirmed that when pancreatic islet cells were transplanted along with a REP after being reacted with the REP, a much larger initial decrease in blood glucose level was exhibited and the reduced blood glucose level was maintained for a longer period of time. It was also confirmed that body weight reduced by diabetes induction continued to increase.

Example 8

Analysis of Real-Time Survival Rate of Pancreatic Islet Cells

To examine the real-time survival rate of the transplanted pancreatic islet cells, fluorescence images of mice, into which pancreatic islet cells fluorescently stained with DiR had been transplanted, were serially acquired and measured using a small animal optical imaging system (IVIS system, PerkinElmer) on day 1, day 5, day 7, day 10, and day 14. In addition, total radiant efficiency was calculated by analyzing fluorescence signals using Living Image software.

As illustrated in FIGS. 7A and 7B, it was confirmed that compared to when only pancreatic islet cells were transplanted into the diabetes-induced mice, the REP-treated pancreatic islet cells maintained a higher survival rate for 7 days after transplantation. It was confirmed that although the survival rate of the transplanted pancreatic islet cells was reduced after 7 days, the survival rate of the pancreatic islet cells transplanted along with the REP after being treated therewith was maintained higher compared to when only pancreatic islet cells were transplanted.

Statistical Processing

The experimental results of all the examples of the present invention were expressed as mean±standard error, and variables were analyzed using a Duncan's test. $P<0.05$ was considered statistically significant, and all experiments were performed independently three times or more for statistical processing.

A pharmaceutical composition for treating diabetes of the present invention, which includes a pancreatic islet cell; and an elastin-like artificial extracellular matrix (REP) prepared by repeated fusion of an elastin-like polypeptide and a ligand, increases the survival rate of pancreatic islet cells after transplantation, rapidly restores a blood glucose level to normal, and enables long-term maintenance of the blood glucose level. Thus, a method of transplanting pancreatic islet cells by using an elastin-like artificial extracellular matrix provides potential as a transplantation tool for treating type 1 diabetes, thus being industrially applicable.

The invention claimed is:

1. A method for treating diabetes, the method comprising administering to an individual having diabetes a pharmaceutical composition comprising:

a pancreatic islet cell; and an elastin-like artificial extracellular matrix (REP) prepared through repeated fusion of an elastin-like polypeptide and a ligand, wherein the elastin-like artificial extracellular matrix is $[VGRGD(VGVPG)_6]_n$ where n=10, 12, 15, or 20 (SEQ ID NO: 4), and wherein the pancreatic islet cell is a cell which was reacted with a solution of $[VGRGD(VGVPG)_6]_n$ where n=10, 12, 15, or 20 (SEQ ID NO: 4).

2. The method of claim 1, wherein the pancreatic islet cell is isolated from any one individual selected from the group consisting of a human, a mouse, a rat, a pig, a rabbit, a guinea pig, a hamster, a dog, a cat, a cow, and a goat.

3. The method of claim 1, wherein the pharmaceutical composition comprises: 800 to 2,000 pancreatic islet cells; and 0.5 μM to 10 μM of an elastin-like artificial extracellular matrix.

4. The method of claim 1, wherein the individual has type 1 diabetes.

* * * * *